US008603832B2

(12) United States Patent
Whitesides et al.

(10) Patent No.: US 8,603,832 B2
(45) Date of Patent: *Dec. 10, 2013

(54) LATERAL FLOW AND FLOW-THROUGH BIOASSAY DEVICES BASED ON PATTERNED POROUS MEDIA, METHODS OF MAKING SAME, AND METHODS OF USING SAME

(71) Applicant: President and Fellows of Harvard College, Cambridge, MA (US)

(72) Inventors: George M. Whitesides, Newton, MA (US); Scott T. Phillips, Cambridge, MA (US); Andreas W. Martinez, Cambridge, MA (US); Manish J. Butte, Boston, MA (US); Amy Wong, Saratoga, CA (US); Samuel W. Thomas, Boston, MA (US); Hayat Sindi, Cambridge (GB); Sarah J. Vella, Ontario (CA); Emanuel Carrilho, Chestnut Hill, MA (US); Katherine A. Mirica, Waltham, MA (US); Yanyan Liu, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/730,028

(22) Filed: Dec. 28, 2012

(65) Prior Publication Data

US 2013/0128036 A1    May 23, 2013

Related U.S. Application Data

(63) Continuation of application No. 12/425,121, filed on Apr. 16, 2009, now Pat. No. 8,377,710, which is a continuation of application No. PCT/US2007/081848, filed on Oct. 18, 2007.

(60) Provisional application No. 60/852,751, filed on Oct. 18, 2006, provisional application No. 60/914,252, filed on Apr. 26, 2007.

(51) Int. Cl.
*G01N 21/77*    (2006.01)

(52) U.S. Cl.
USPC .......... 436/169; 436/164; 436/168; 436/518; 436/530; 422/420; 422/425; 422/430

(58) Field of Classification Search
None
See application file for complete search history.

(56) References Cited

U.S. PATENT DOCUMENTS 4,618,475 A    10/1986    Wang
4,668,564 A    5/1987    Orchard (Continued)

FOREIGN PATENT DOCUMENTS

EP    2143491    1/2010
JP    08233799 A    9/1996

(Continued)

OTHER PUBLICATIONS

Aikio et al., "Bioactive Paper and Fibre Products: Patent and Literary Survey," VTT Working Papers 51, VTT-Work-51, 2006, 84 pages.

(Continued)

*Primary Examiner* — Robert Xu
(74) *Attorney, Agent, or Firm* — Wilmer Cutler Pickering Hale and Dorr LLP

(57)    ABSTRACT

Embodiments of the invention provide lateral flow and flow-through bioassay devices based on patterned porous media, methods of making same, and methods of using same. Under one aspect, an assay device includes a porous, hydrophilic medium; a fluid impervious barrier comprising polymerized photoresist, the barrier substantially permeating the thickness of the porous, hydrophilic medium and defining a boundary of an assay region within the porous, hydrophilic medium; and an assay reagent in the assay region.

21 Claims, 24 Drawing Sheets

(56) References Cited

U.S. PATENT DOCUMENTS

| | | | |
|---|---|---|---|
| 4,668,619 A | 5/1987 | Greenquist et al. |
| 4,743,530 A | 5/1988 | Farid et al. |
| 4,757,004 A | 7/1988 | Houts et al. |
| 4,861,711 A | 8/1989 | Friesen et al. |
| 5,120,544 A | 6/1992 | Henley |
| 5,173,262 A | 12/1992 | Burtis et al. |
| 5,209,904 A | 5/1993 | Forney et al. |
| 5,266,179 A | 11/1993 | Nankai et al. |
| 5,279,944 A | 1/1994 | Fabrizi et al. |
| 5,409,664 A | 4/1995 | Allen |
| 5,648,252 A | 7/1997 | Dumitriu et al. |
| 5,707,818 A | 1/1998 | Chudzik et al. |
| 5,804,452 A | 9/1998 | Pronovost et al. |
| 5,834,226 A | 11/1998 | Maupin |
| 5,858,392 A | 1/1999 | Dumitriu et al. |
| 5,869,172 A | 2/1999 | Caldwell |
| 5,897,522 A | 4/1999 | Nitzan |
| 5,906,934 A | 5/1999 | Grande et al. |
| 5,925,259 A | 7/1999 | Biebuyck et al. |
| 5,941,862 A | 8/1999 | Haynes et al. |
| 6,004,442 A | 12/1999 | Choulga et al. |
| 6,025,203 A | 2/2000 | Vetter et al. |
| 6,060,534 A | 5/2000 | Ronan et al. |
| 6,180,239 B1 | 1/2001 | Whitesides et al. |
| 6,202,471 B1 | 3/2001 | Yadav et al. |
| 6,210,907 B1 | 4/2001 | Cha |
| 6,284,072 B1 | 9/2001 | Ryan et al. |
| 6,319,310 B1 | 11/2001 | Wong et al. |
| 6,391,523 B1 | 5/2002 | Hurditch et al. |
| 6,416,642 B1 | 7/2002 | Alajoki et al. |
| 6,440,645 B1 | 8/2002 | Yon-Hin et al. |
| 6,440,725 B1 | 8/2002 | Pourahmadi et al. |
| 6,478,938 B1 | 11/2002 | Paek et al. |
| 6,555,390 B2 | 4/2003 | Chandler |
| 6,566,575 B1 | 5/2003 | Stickels et al. |
| 6,642,408 B2 | 11/2003 | Batlaw et al. |
| 6,761,962 B2 | 7/2004 | Bentsen et al. |
| 6,783,735 B2 | 8/2004 | Vanmaele et al. |
| 6,816,125 B2 | 11/2004 | Kuhns et al. |
| 6,844,200 B2 | 1/2005 | Brock |
| 6,877,892 B2 | 4/2005 | Karp |
| 6,880,576 B2 | 4/2005 | Karp et al. |
| 6,887,701 B2 | 5/2005 | Anderson et al. |
| 6,919,046 B2 | 7/2005 | O'Connor et al. |
| 6,931,523 B1 | 8/2005 | Tomoson et al. |
| 6,935,772 B2 | 8/2005 | Karp et al. |
| 6,951,682 B1 | 10/2005 | Zebala |
| 6,951,757 B2 | 10/2005 | Sabatini |
| 6,989,128 B2 | 1/2006 | Alajoki et al. |
| 7,008,799 B1 | 3/2006 | Zimmer et al. |
| 7,186,352 B2 | 3/2007 | Morse et al. |
| 7,192,693 B2 | 3/2007 | Bryant |
| 7,291,857 B2 | 11/2007 | Tanaka et al. |
| 7,303,923 B2 | 12/2007 | Hardman et al. |
| 8,206,992 B2 | 6/2012 | Reches et al. |
| 8,377,710 B2 | 2/2013 | Whitesides |
| 2002/0187074 A1 | 12/2002 | O'Connor et al. |
| 2002/0187560 A1 | 12/2002 | Pezzuto et al. |
| 2003/0032203 A1 | 2/2003 | Sabatini et al. |
| 2003/0148401 A1 | 8/2003 | Agrawal et al. |
| 2004/0067166 A1 | 4/2004 | Karinka et al. |
| 2004/0103808 A1 | 6/2004 | Lochun et al. |
| 2004/0119070 A1 | 6/2004 | Roach et al. |
| 2005/0136501 A1 | 6/2005 | Kuriger |
| 2005/0145496 A1 | 7/2005 | Goodsaid et al. |
| 2005/0169962 A1 | 8/2005 | Bhatia et al. |
| 2005/0196702 A1 | 9/2005 | Bryant et al. |
| 2005/0266582 A1 | 12/2005 | Modlin et al. |
| 2006/0014003 A1 | 1/2006 | Libera et al. |
| 2006/0038182 A1 | 2/2006 | Rogers et al. |
| 2006/0088857 A1 | 4/2006 | Attiya et al. |
| 2006/0130054 A1 | 6/2006 | Bocking et al. |
| 2006/0226575 A1 | 10/2006 | Maghribi et al. |
| 2007/0154355 A1 | 7/2007 | Berndt et al. |
| 2007/0179117 A1 | 8/2007 | Reiner et al. |
| 2007/0196819 A1 | 8/2007 | Asberg et al. |
| 2007/0224701 A1 | 9/2007 | Rosenstein |
| 2007/0278097 A1 | 12/2007 | Bhullar et al. |
| 2007/0298433 A1 | 12/2007 | Sia et al. |
| 2009/0298191 A1 | 12/2009 | Whitesides et al. |
| 2011/0111517 A1 | 5/2011 | Siegel et al. |
| 2011/0123398 A1 | 5/2011 | Carrilho et al. |
| 2011/0189786 A1 | 8/2011 | Reches et al. |
| 2012/0181184 A1 | 7/2012 | Whitesides et al. |
| 2012/0198684 A1 | 8/2012 | Carrilho et al. |

FOREIGN PATENT DOCUMENTS

| | | |
|---|---|---|
| WO | WO-97/48257 | 12/1997 |
| WO | WO-99/46644 | 9/1999 |
| WO | WO-00/33078 | 6/2000 |
| WO | WO-01/02093 A2 | 1/2001 |
| WO | WO-01/25138 | 4/2001 |
| WO | WO-03/015890 A1 | 2/2003 |
| WO | WO-2004/006291 A2 | 1/2004 |
| WO | WO-2004/080138 | 9/2004 |
| WO | WO-2005/090975 | 9/2005 |
| WO | WO-2005/090983 A2 | 9/2005 |
| WO | WO-2005/107938 | 11/2005 |
| WO | WO-2005/109005 A1 | 11/2005 |
| WO | WO-2006/018044 | 2/2006 |
| WO | WO-2006/076703 | 7/2006 |
| WO | WO-2007/029250 | 3/2007 |
| WO | WO-2007/081848 | 7/2007 |
| WO | WO-2007/116056 | 10/2007 |
| WO | WO-2008/049083 | 4/2008 |
| WO | WO-2009/120963 | 10/2009 |
| WO | WO-2009/121037 A2 | 10/2009 |
| WO | WO-2009/121038 | 10/2009 |
| WO | WO-2009/121041 A2 | 10/2009 |
| WO | WO-2009/121043 A2 | 10/2009 |
| WO | WO-2010/022324 | 2/2010 |
| WO | WO-2010/102279 A1 | 9/2010 |
| WO | WO-2010/102294 A1 | 9/2010 |
| WO | WO-2011/097412 | 8/2011 |

OTHER PUBLICATIONS

Author Unknown, "Focus: Lab on Paper, DOI: 10.1039/b814043j," Lab Chip, vol. 8, No. 12, Dec. 2008, pp. 1988-1991, XP002585318, The Royal Society of Chemistry.

Berggren et al., "Paper Electronics and Electronic Paper," IEEE, Section 12: Flexible Systems, 2001, pp. 300-303.

Bracher, et al., "Heterogeneous Films of Ionotropic Hydrogels Fabricated from Delivery Templates of Patterned Paper," Adv. Mater., 2008, 5 pages.

Brooks et al., "A Simple Artificial Urine for the Growth of Urinary Pathogens," Lett. Appl. Microbiol., 1997, 24, pp. 203-206.

Bruzewicz et al., "Low-Cost Printing of Poly(dimethylsiloxane) Barriers to Define Microchannels in Paper," Anal. Chem., 2008, 80, pp. 3387-3392.

Bruzewicz et al., "Paper: Fabrication of a Modular Tissue Construct in a Microfluidic Chip," Lab Chip, 2008, 8, pp. 663-671.

Campana et al., "Double and Triple Staining Methods for Studying the Proliferative Activity of Human B and T Lymphoid Cells," Journal of Immunological Methods, 107, 1988, pp. 79-88.

Carrilho et al., "Paper Microzone Plates," Analytical Chemistry, vol. 81, No. 15, Aug. 2009, pp. 5990-5998.

Carrilho et al., "Understanding Wax Printing: A Simple Micropatterning Process for Paper-Based Microfluidics," Analytical Chemistry, vol. 81, No. 16, Aug. 2009, pp. 7091-7095.

Chadee et al., "Increased Phosphorylation of Histone H1 in Mouse Fibroblasts Transformed with Oncogenes or Constitutively Active Mitogen-Activated Protein Kinase Kinase," The Journal of Biological Chemistry, vol. 270, No. 34, Aug. 1995, pp. 20098-20105.

Cheng et al., "Clinical Analytics: Paper-Based ELISA**," Agnew. Chem., 2010, 122, pp. 1-5.

Chin et al., "Lab-on-a-chip Devices for Global Health: Past Studies and Future Opportunities," Lab Chip, 2007, 7, pp. 41-57, A Journal of the Royal Society of Chemistry.

(56) References Cited

OTHER PUBLICATIONS

Costerton et al., "Bacterial Biofilms: a Common Cause of Persistent Infections," Science Mag., 1999, pp. 1318-1322.

Daar et al., "Top Ten Biotechnologies for Improving Health in Developing Countries," Nature Genetics, vol. 32, Oct. 2002, pp. 229-232.

Derda et al., "Paper-supported 3D Cell Culture for Tissue-Based Bioassays," PNAS, vol. 106, No. 44, Nov. 2009, pp. 18457-18462.

Donlan "Biofilm Formation: A Clinically Relevant Microbiological Process," Healthcare Epidemiology, CID 2001:33, Oct. 2001, pp. 1387-1392.

Donlan et al., "Biofilm Formation on Cast Iron Substrata in Water Distribution Systems," Wat. Res. vol. 28, No. 6, pp. 1497-1503, 1994.

Donlan et al., "Reviews: Biofilms: Survival Mechanisms of Clinically Relevant Microorganisms," Clinical Microbiology Reviews, vol. 15, No. 2, Apr. 2002, pp. 167-193.

Dungchai et al., "Electrochemical Detection for Paper-Based Microfluidics," Anal. Chem., 2009, 81, pp. 5821-5826.

Ebeling, "The Permanent Life of Connective Tissue Outside of the Organism," J. Exp. Med., 17, 1913, 15 pages.

Harrison et al., "Methodology Article: High-Throughput Metal Susceptibility Testing of Microbial Biofilms," BMC Microbiology, 2005, 5:53, 11 pages.

International Search Report and Written Opinion of the International Searching Authority, the European Patent Office, for International Application No. PCT/US2007/081848, dated Jan. 28, 2009, 12 pages.

International Search Report and Written Opinion of the International Searching Authority, the European Patent Office, for PCT/US2010/026499, dated Jun. 16, 2010, 2 pages.

International Search Report and Written Opinion of the International Searching Authority, the Korean Intellectual Property Office, for International Application No. PCT/US2009/038566, dated Dec. 16, 2009, 10 pages.

International Search Report and Written Opinion of the International Searching Authority, the Korean Intellectual Property Office, for International Application No. PCT/US2009/038694 dated Nov. 12, 2009, 10 pages.

International Search Report and Written Opinion of the International Searching Authority, the Korean Intellectual Property Office, for PCT/US2009/038693, dated Oct. 28, 2009, 8 pages.

International Search Report and Written Opinion of the International Searching Authority, the Korean Intellectual Property Office, for PCT/US2009/038699, dated Oct. 28, 2009, 9 pages.

International Search Report and Written Opinion of the International Searching Authority, the Korean Intellectual Property Office, for PCT/US2009/038702, dated Nov. 11, 2009, 7 pages.

International Search Report of the International Searching Authority, the European Patent Office, for PCT/US2010/026547, dated Jul. 19, 2010, 3 pages.

International Search Report of the International Searching Authority, the Korean Intellectual Property Office, for PCT/US2009/054601, dated Mar. 22, 2010, 2 pages.

Klajn et al., "Multicolour Micropatterning of Thin Films and Dry Gels," Nature Materials, vol. 3, Oct. 2004, pp. 729-735.

Lahav et al., "DOI: 10.1002/adma.200601843—Patterning of Poly(acrylic acid) by Ionic Exchange Reactions in Microfluidic Channels**," Advanced Materials, 2006, 18, pp. 3174-3178.

Leary et al., "Rapid and Sensitive Colorimetric Method for Visualizing Biotin-Labeled DNA Probes Hybridized to DNA or RNA Immobilized on Nitrocellulose: Bio-Blots," PNAS, vol. 80, No. 13, 1983, pp. 4045-4049.

Li et al., "Thread as a Versatile Material for Low-Cost Microfluidic Diagnostics," Applied Materials & Interfaces, vol. 2, No. 1, Jan. 2010, 6 pages.

Liu et al., "Three-Dimensional Photopatterning of Hydrogels Containing Living Cells," Biomed. Microdevices, 2002, 4, pp. 257-266.

Lu et al., "Short Communication: Rapid Prototyping of Paper-Based Microfluidics with Wax for Low-Cost, Portable Bioassay," Electrophoresis, 2009, 30, pp. 1497-1500.

Mabey et al., "Diagnostics for the Developing World," Nature Reviews / Microbiology, vol. 2, Mar. 2004, pp. 231-240.

Martinez et al., "Diagnostics for the Developing World: Microfluidic Paper-Based Analytical Devices," Analytical Chemistry, vol. 82, No. 1, Jan. 2010, pp. 3-10.

Martinez et al., "FLASH: A Rapid Method for Prototyping Paper-Based Microfluidic Devices," Lab Chip, 2008, 8, pp. 2146-2150, A Journal of the Royal Society of Chemistry.

Martinez et al., "Paper: Programmable Diagnostic Devices Made from Paper and Tape," Lab Chip, Jul. 2010, 6 pages.

Martinez et al., "Patterned Paper as a Platform for Inexpensive, Low-Volume, Portable Bioassays**," Agnew. Chem. Int. Ed., 2007, 46, pp. 1318-1320.

Martinez et al., "Simple Telemedicine for Developing Regions: Camera Phones and Paper-Based Microfluidic Devices for Real-Time, Off-Site Diagnosis," Analytical Chemistry, vol. 80, No. 10, May 2008, pp. 3699-3707.

Martinez et al., "Three-Dimensional Microfluidic Devices Fabricated in Layered Paper and Tape," PNAS, vol. 105, No. 50, Dec. 2008, pp. 19606-19611.

Matsumoto et al., "Three-Dimensional Cell and Tissue Patterning in a Strained Fibrin Gel System," PLoS One, Nov. 2007, Issue No. 11, 6 pages.

Nelson et al., "Three-Dimensional Lithographically Defined Organotypic Tissue Arrays for Quantitative Analysis of Morphogenesis and Neoplastic Progression," Nature Protocols, vol. 3, No. 4, 2008, pp. 674-678.

Nie et al., "Paper: Integration of Paper-based Microfluidic Devices with Commercial Electrochemical Readers," Lab Chip, Oct. 2010, 7 pages.

Peele et al., "Semi-Automated vs. Visual Reading of Urinalysis Dipsticks," Clin. Chem, 1977, 23, pp. 2242-2246.

Pugia et al., "High-Sensitivity Dye Binding Assay for Albumin in Urine," J. Clin. Lab. Anal. 1999, 13, pp. 180-187.

Reches et al., "Thread as a Matrix for Biomedical Assays," Applied Materials & Interfaces, vol. xxx, No. xx, 000, xxxx, pp. A-G, 2010.

Shaw et al., "Negative Photoresists for Optical Lithography," IBM Journal of Research and Development, vol. 41, No. 1/2, Jan./Mar. 1997, pp. 81-94, 15 pages.

Shimizu et al., "Biofilm Formation on Hydrophilic Intraocular Lens Material," Current Eye Research, 31, 2006, pp. 989-997.

Sia et al., "Microfluidic Devices Fabricated in Poly(dimethylsiloxane) for Biological Studies," Electrophoresis, 2003, 24, pp. 3563-3576.

Siegel, et al., "Foldable Printed Circuit Boards on Paper Substrates," Advanced Functional Materials, 2010, 20, pp. 28-35.

Smith S.K., "Angiogenesis, Vascular Endothelial Growth Factor and the Endometrium," Hum. Reprod. Update 1998, 4, pp. 509-519.

Supplementary European Search Report and Written Opinion for European Application No. 09724164 dated Mar. 16, 2011, 7 pages.

Tang et al., "Molding of Three-Dimensional Microstructures of Geis," J. Am. Chem. Soc., 2003, 125, pp. 12988-12989.

Urbich et al., "Endothelial Progenitor Cells: Characterization and Role in Vascular Biology," Circulation Research, DOI: 10.1161/01.Res.0000137877.89448.78, Aug. 2004, pp. 343-353.

von Lode P., "Point-of-care Immunotesting: Approaching the Analytical Performance of Central Laboratory Methods," Clinical Biochemistry, 38, 2005, pp. 591-606.

Washburn E. W., "The Dynamics of Capillary Flow," The Physical Review, vol. XVII, No. 3, Second Series, Mar. 1921, pp. 273-283.

Winkleman et al., "Patterning micron-sized features in a cross-linked poly (acrylic acid) film by a wet etching process," The Royal Society of Chemistry, 2007, pp. 108-116.

Xerox Corporation, "Material Safety Data Sheet for Xerox Phaser 6250 Color Laser Toner," 2003, pp. E-1-E-5, retrieved from http://www.office.xerox.com/userdoc/P6250/6250_Web/pdfs/msds.pdf, 1 page.

Zhi et al., "Multianalyte Immunoassay with Self-Assembled Addressable Microparticle Array on a Chip," Analytical Biochemistry, vol. 318, No. 2, Jul. 2003, pp. 236-243.

(56) References Cited

OTHER PUBLICATIONS

Zhu et al., "Research Article: Proposal to Create Subspecies of *Rickettsia conorii* Based on Multi-Locus Sequence Typing and an Emended Description of *Rickettsia conorii*," BMC Microbiology, 2005, 5:11, 11 pages.

Muller et al., "Automatic Paper Chromatography," Analytical Chemistry, vol. 21, No. 9, Sep. 1949, pp. 1123-1125.

Müller et al., "Automatic Paper Chromatography," Analytical Chemistry, vol. 21, No. 9, Sep. 1949, pp. 1123-1125.

exposed to an artificial urine solution exposed to an artificial urine solution containing glucose and protein Dirt Plant Pollen 1 cm  Graphite

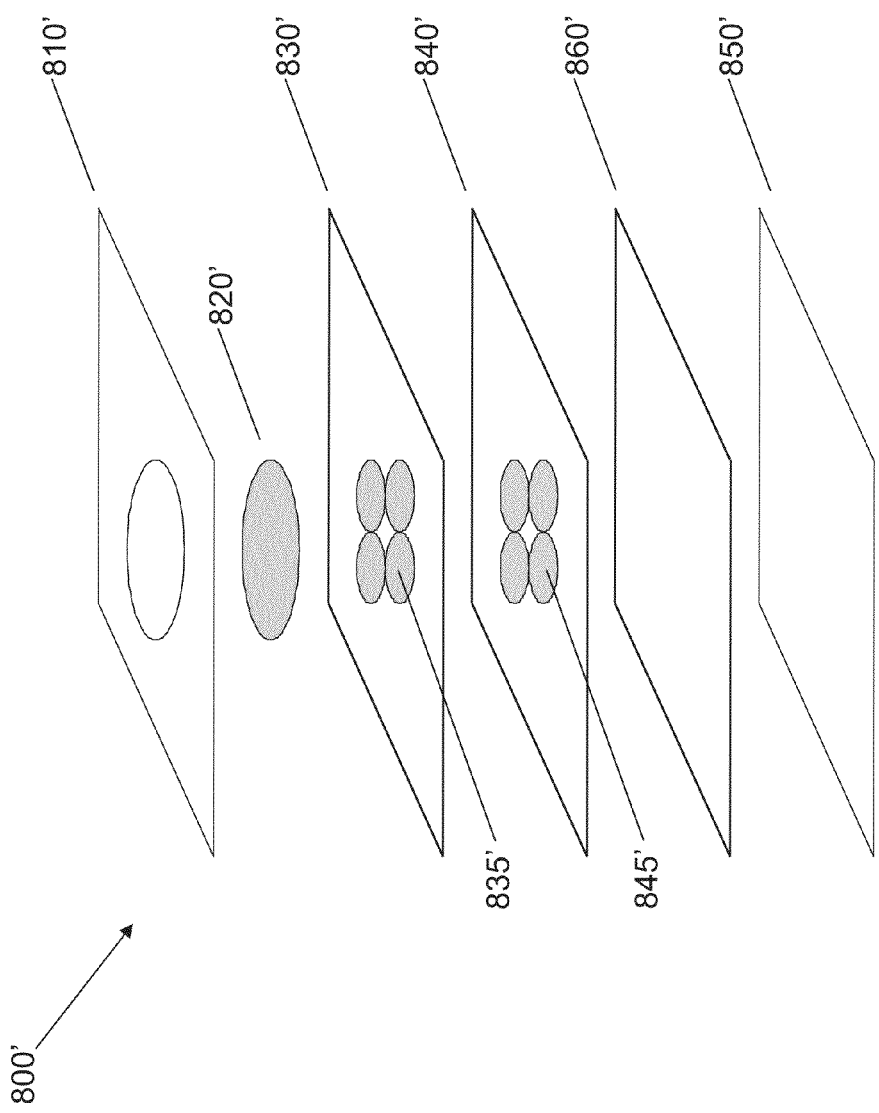

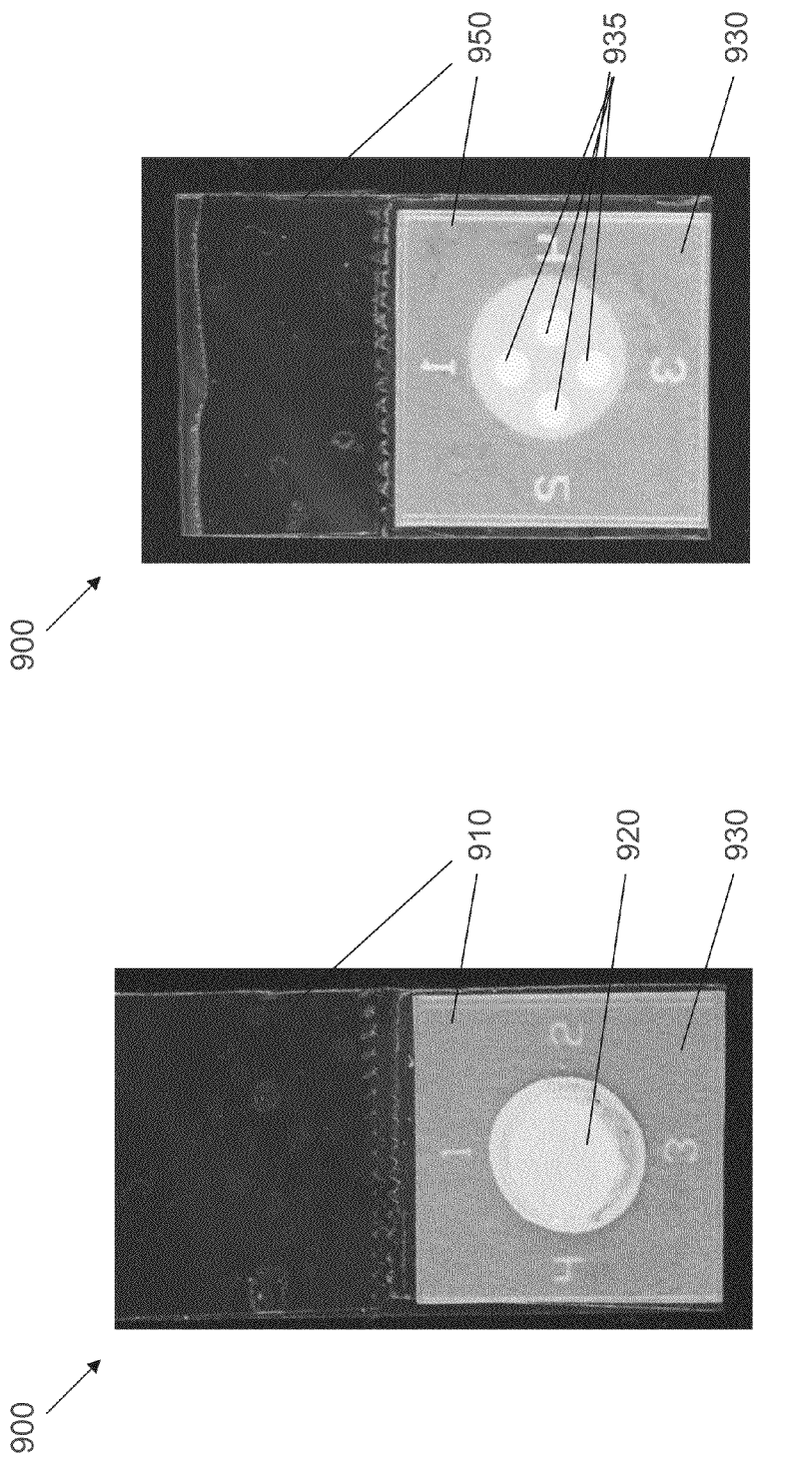

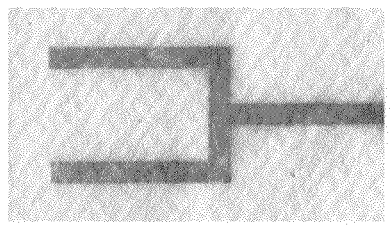
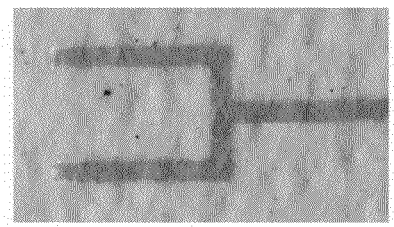
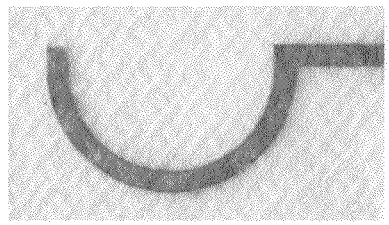
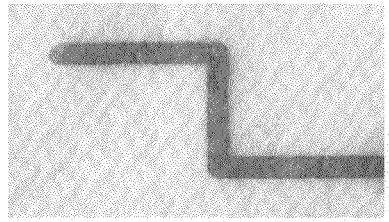
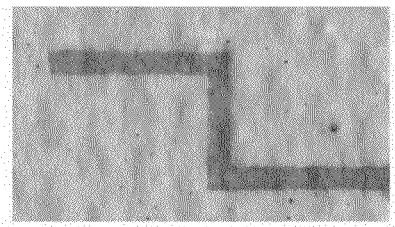
Fig. 14

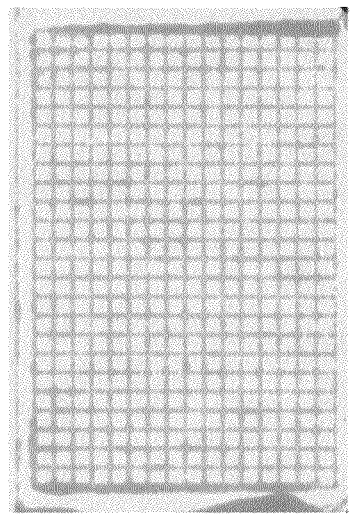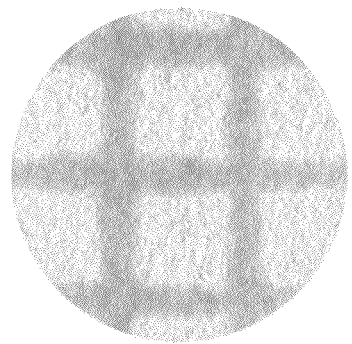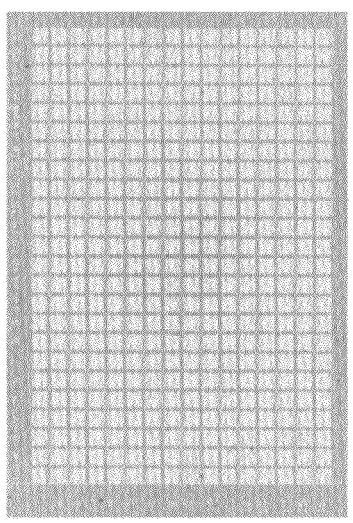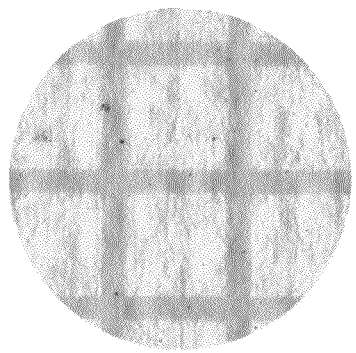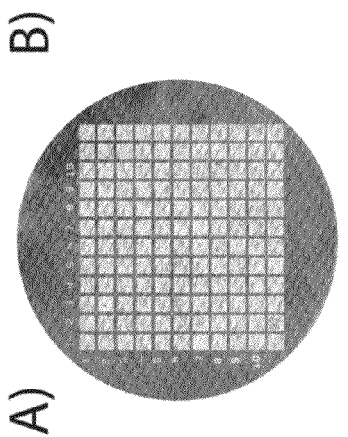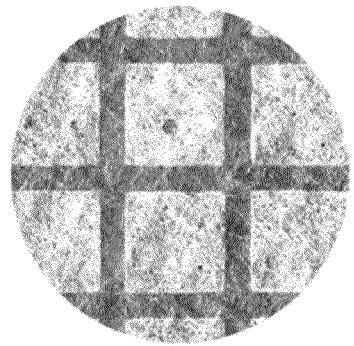
Fig. 15

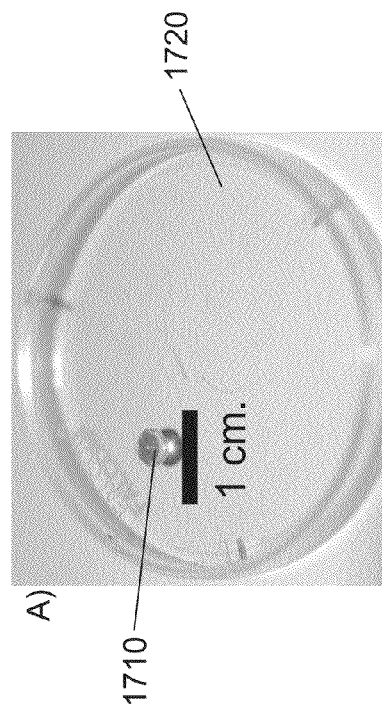
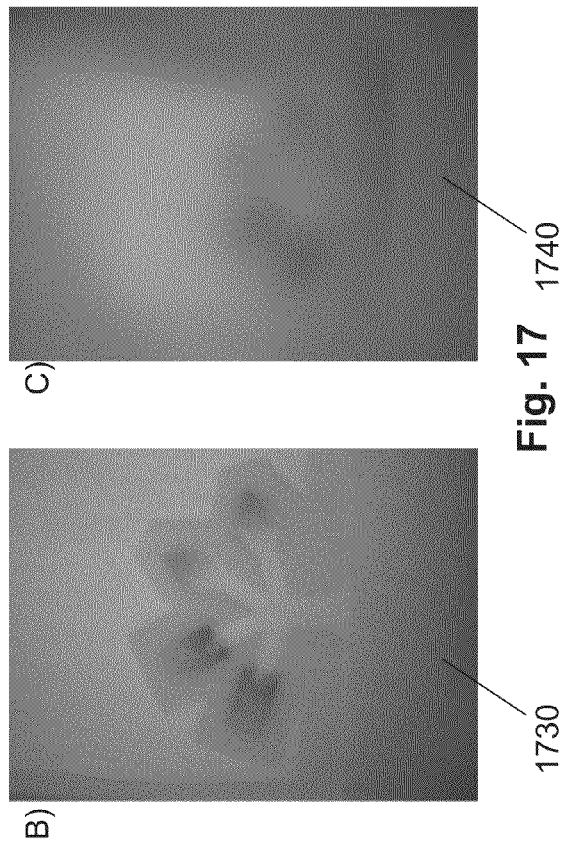
Fig. 17

LATERAL FLOW AND FLOW-THROUGH BIOASSAY DEVICES BASED ON PATTERNED POROUS MEDIA, METHODS OF MAKING SAME, AND METHODS OF USING SAME

RELATED APPLICATIONS

This application is a continuation of U.S. patent application Ser. No. 12/425,121, filed Apr. 16, 2009, which claims the benefit of priority under 35 U.S.C. §120 of Patent Cooperation Treaty Application No. US2007/081,848, filed Oct. 18, 2007, designating the United States and entitled "Lateral Flow and Flow-through Bioassay Based on Patterned Porous Media, Methods of Making Same, and Methods of Using Same," which claims the benefit of priority under 35 U.S.C. §119(e) to U.S. Provisional Patent Application No. 60/852,751, filed Oct. 18, 2006, entitled "Patterned Paper as a Platform for Inexpensive, Low Volume, Portable Bioassays and Methods of Making Same," and U.S. Provisional Patent Application No. 60/914,252, filed Apr. 26, 2007, entitled "Patterned Paper as a Platform for Inexpensive, Low Volume, Portable Bioassays and Methods of Making Same," the entire contents of which are incorporated herein by reference.

STATEMENT OF GOVERNMENT SUPPORT

This research was supported by the National Institutes of Health (NIH) (GM065364), and the Materials Research Science and Engineering Centers (MRSEC) shared facilities supported by the National Science Foundation (NSF) under award no. DMR-0213805. This work was also supported by a predoctoral fellowship from NSF. The U.S. Government may have certain rights in this invention.

BACKGROUND OF THE INVENTION

This disclosure generally relates to bioassay devices based on porous media, methods of making same, and methods of using same.

The analysis of biological fluids is useful for monitoring the health of individuals and populations. However, these measurements can be difficult to implement in remote regions such as those found in developing countries, in emergency situations, or in home health-care settings. Conventional laboratory instruments provide quantitative measurements of biological samples, but they are typically unsuitable for remote locations since they are large, expensive, and typically require trained personnel and considerable volumes of biological samples.

Other types of bioassay platforms provide alternatives to conventional instruments, but they also have limitations in certain situations. For example, microfluidic devices can be useful in biological and chemical screening. Both glass and polymer-based microfluidic devices containing wells and/or channels have been developed. However, conventional microfluidic devices—even when designed to be simple—typically require pumps and external detectors for use.

While "dipsticks" are conceptually straightforward, they are generally too expensive for low-cost settings, and generally require a relatively large volume of sample in order to be able to make an accurate measurement, e.g., about 5 mL of sample. Such large volumes of samples are not obtained easily in many situations, particularly from premature infants and young children.

SUMMARY OF INVENTION

Under one aspect, a bioassay includes a porous hydrophilic medium capable of transporting fluids by capillary action; and a fluid impervious barrier embedded in the porous hydrophilic medium, said barrier defining a channel terminating in one or more detection regions in the porous medium. In one or more embodiments, the porous hydrophilic medium is treated to provide a visible indication of an analyte present in a fluid.

Under one aspect, an assay device includes a porous, hydrophilic medium; a fluid impervious barrier comprising polymerized photoresist, the barrier substantially permeating the thickness of the porous, hydrophilic medium and defining a boundary of an assay region within the porous, hydrophilic medium; and an assay reagent in the assay region.

One or more embodiments include one or more of the following features. The barrier further defines a boundary of a channel region within the porous, hydrophilic medium, the channel region fluidically connected to the assay region. The barrier further defines a boundary of a sample deposition region within the porous, hydrophilic medium, the channel providing a fluidic pathway within the porous, hydrophilic medium between the sample deposition region and the assay region. The barrier further defines boundaries of a plurality of assay regions. The barrier further defines boundaries of a plurality of channel regions within the porous, hydrophilic medium and further defines a boundary of a sample deposition region, each channel providing a fluidic pathway within the porous, hydrophilic medium between the sample deposition region and a corresponding assay region of the plurality of assay regions. Assay reagents in at least some of the assay regions. The barrier physically separates the assay regions of the plurality of assay regions from one another. The assay reagent is covalently bonded to the porous, hydrophilic medium in the assay region. The assay reagent is noncovalently bonded to the porous, hydrophilic medium in the assay region. The assay reagent is selected to provide a visible indication of the presence of analyte. The assay reagent is selected to react to the presence of at least one of glucose, protein, fat, vascular endothelial growth factor, insulin-like growth factor 1, antibodies, and cytokines. The photoresist comprises negative photoresist. The porous, hydrophilic medium comprises one of nitrocellulose acetate, cellulose acetate, cellulosic paper, filter paper, tissue paper, writing paper, paper towel, cloth, and porous polymer film. The porous, hydrophilic medium is flexible. The barrier has at least one dimension between about 5 cm and about 100 μm. The barrier has at least one dimension between about 300 μm and about 100 μm. The barrier has at least one dimension less than about 300 μm. The channel has at least one lateral dimension that is between about 750 μm and about 100 μm. The channel has at least one lateral dimension that is between about 250 μm and about 100 μm. The channel has at least one lateral dimension that is less than about 250 μm. An imaging device capable of obtaining a digital image of the assay region. A processor in communication with the imaging device and capable of obtaining information about an analyte in the assay region based on the digital image of the assay region. The processor is capable of obtaining the information about the analyte based on an intensity in the digital image of the assay region. A layer over the porous hydrophilic medium, the layer including at least one aperture. The aperture provides at least part of a fluidic pathway to the assay region.

Under another aspect, an assay device includes a porous, hydrophilic medium; a fluid impervious barrier substantially permeating the thickness of the porous, hydrophilic medium and having a width between about 1 mm and about 100 μm, the barrier completely defining a boundary of an assay region within the porous, hydrophilic medium; and an assay reagent in the assay region.

One or more embodiments include one or more of the following features. The assay reagent is selected to provide a visible indication of the presence of analyte. The assay reagent is selected to react to the presence of at least one of glucose, protein, fat, vascular endothelial growth factor, insulin-like growth factor 1, antibodies, and cytokines. The barrier comprises one of photoresist and curable polymer. The porous, hydrophilic medium comprises one of nitrocellulose acetate, cellulose acetate, cellulosic paper, filter paper, tissue paper, writing paper, paper towel, cloth, and porous polymer film. The barrier has at least one lateral dimension between about 300 μm and about 100 μm. The barrier has at least one lateral dimension less than about 300 μm. A plurality of fluid impervious barriers substantially permeating the thickness of the porous, hydrophilic medium, each barrier having a width between about 1 mm and about 100 μm, each barrier each completely defining a boundary of a corresponding assay region within the porous, hydrophilic medium; and an assay reagent in each assay region.

Under another aspect, an assay device includes a porous, hydrophilic medium; a fluid impervious barrier substantially permeating the thickness of the porous, hydrophilic medium and having a length and a width that varies by less than about 10% along the length of the barrier, the barrier defining a boundary of an assay region within the porous, hydrophilic medium, and an assay reagent in the assay region.

One or more embodiments include one or more of the following features. The barrier further defines a boundary of a channel region within the porous, hydrophilic medium, the channel region fluidically connected to the assay region. The barrier further defines a boundary of a sample deposition region within the porous, hydrophilic medium, the channel providing a fluidic pathway within the porous, hydrophilic medium between the sample deposition region and the assay region. The assay reagent is selected to provide a visible indication of the presence of analyte. The assay reagent is selected to react to the presence of one of glucose, protein, fat, vascular endothelial growth factor, insulin-like growth factor 1, antibodies, and cytokines. The barrier comprises one of photoresist and curable polymer. The porous, hydrophilic medium comprises one of nitrocellulose acetate, cellulose acetate, cellulosic paper, filter paper, tissue paper, writing paper, paper towel, cloth, and porous polymer film. The barrier width is less than about 300 μm. The barrier width varies by less than about 5% along the length of the barrier. The channel region has at a width between about 750 μm and about 100 μm. The channel region has a length and a width that varies by less than about 10% along the length of the channel. The channel region has a length and a width that varies by less than about 5% along the length of the channel.

Under another aspect, a method of making a device includes saturating a porous, hydrophilic medium with photoresist; exposing the saturated medium to a pre-determined pattern of light; removing the photoresist from a region of the medium based on the pre-determined pattern of light to define a barrier of residual photoresist that forms a boundary of the region, wherein the pre-determined pattern of light is selected so that the barrier defines an assay region in the region; and providing an assay reagent in the assay region.

One or more embodiments include one or more of the following features. The barrier is substantially fluid impervious. Selecting the pre-determined pattern of light so that the barrier completely encompasses the region. Selecting the pre-determined pattern of light so that the barrier borders a first portion of the region, and wherein an edge of the porous, hydrophilic medium borders a second portion of the region.

Providing the reagent comprises covalently binding the reagent to the assay region. Providing the reagent comprises noncovalently binding the reagent to the assay region. Selecting wherein the pre-determined pattern of light so that the assay region has a shape based on transport characteristics of the reagent in the presence of a liquid. The assay reagent is selected to provide a visible indication of the presence of analyte. The assay reagent is selected to react to the presence of one of glucose, protein, fat, vascular endothelial growth factor, insulin-like growth factor 1, antibodies, and cytokines. Selecting the pre-determined pattern of light so that the barrier defines a channel region in the region. The channel region has at least one lateral dimension that is between about 750 μm and about 100 μm. Selecting the pre-determined pattern of light is selected so that the barrier defines a sample deposition region in the region. Saturating the porous, hydrophilic medium with photoresist comprises applying a solution of the photoresist in a solvent to the medium and substantially evaporating the solvent. Exposing the saturated medium to a pre-determined pattern of light comprises irradiating the region with the light and substantially not irradiating the barrier with the light. Exposing the saturated medium to a pre-determined pattern of light comprises irradiating the barrier with the light and substantially not irradiating the region with the light. Removing the photoresist comprises removing the photoresist from a plurality of regions of the medium based on the pre-determined pattern of light to define a plurality of barriers of residual photoresist that form boundaries of corresponding regions. Saturating a second porous, hydrophilic medium with photoresist; exposing the saturated second medium to a pre-determined pattern of light; removing the photoresist from a region of the second medium based on the pre-determined pattern of light to define a barrier of residual photoresist that forms a boundary of the region; substantially aligning the barrier of the second medium with the barrier of the first mentioned medium; and bonding the first medium to the second medium. Applying a reagent in the region of the first medium, the reagent selected to react to a target analyte. Providing one of a labeled antibody and a labeled protein in the region of the second medium, the one of the labeled antibody and the labeled protein selected to provide a color indication of a reaction between the reagent and the target analyte. Providing a layer over the porous, hydrophilic medium, the layer including at least one aperture that is aligned based on a position of the barrier. Selecting the pre-determined pattern of light so that the barrier has at least one dimension that is between about 5 cm and about 100 μm. Selecting the pre-determined pattern of light so that the barrier has at least one dimension that is less than about 250 μm. The porous, hydrophilic medium comprises one of nitrocellulose acetate, cellulose acetate, cellulosic paper, filter paper, tissue paper, writing paper, paper towel, cloth, and porous polymer film. Removing the photoresist from a plurality of regions of the medium based on the pre-determined pattern of light to define a plurality of barriers of residual photoresist that form boundaries of a corresponding plurality of regions, wherein the pre-determined pattern of light is selected so that the plurality of barriers define a corresponding plurality of assay regions in the regions; and providing an assay reagent in at least some of the assay regions.

Under another aspect, a method of making a device includes coating a stamp of pre-determined pattern with a curable polymer; pressing the coated stamp onto a porous, hydrophilic medium, the medium having a thickness and the curable polymer substantially permeating the medium through its thickness in accordance with the pre-determined pattern; curing the curable polymer so as to form a fluid impervious barrier embedded in the medium, the fluid impervious barrier defining an assay region in the medium; and providing a reagent in the assay region.

One or more embodiments include one or more of the following features. The curable polymer comprises poly (dimethyl-siloxane) (PDMS). Selecting the pre-determined pattern so that the barrier completely encompasses the region.

Under another aspect, a method of performing an assay to determine the presence of an analyte in a liquid sample includes depositing the liquid sample on an assay device, the assay device comprising a porous, hydrophilic medium, a fluid impervious barrier comprising polymerized photoresist, the barrier substantially permeating the thickness of the porous, hydrophilic medium and defining a boundary of an assay region within the porous, hydrophilic medium, and an assay reagent in the assay region, the assay reagent selected to provide a visible response to the presence of the analyte; obtaining an image of the assay region; and determining the presence of the analyte in the liquid based on the image of the assay region.

One or more embodiments include one or more of the following features. Determining the presence of the analyte in the liquid comprises obtaining an average intensity of at least a portion of the image of the assay region, and determining the presence of the analyte in the liquid based on the average intensity. Obtaining the image of the assay region comprises imaging the assay region with one of a camera phone, a digital camera, and a scanner. Determining the presence of the analyte based on the image of the assay region comprises transmitting the image to a remote lab, and obtaining information from the remote lab regarding the presence of the analyte in the liquid. Obtaining the image of the assay region comprises imaging the assay region with a camera phone, and wherein determining the presence of the analyte based on the image of the assay region comprises transmitting the image to a remote lab via the camera phone.

BRIEF DESCRIPTION OF DRAWINGS

In the Drawing:

FIGS. 8A and 8B are perspective views of flow-through bioassay devices, according to some embodiments.

FIGS. 9A and 9B are front and back views, respectively, of an exemplary flow-through bioassay device, according to some embodiments.

FIGS. 14A-14B are images of hydrophobic barriers obtained using various methods of patterning, according to some embodiments.

FIGS. 15A-15C are images of grids of approximately 3.6× 3.6 mm squares bounded by patterned hydrophobic barriers into paper formed using various methods of patterning, according to some embodiments.

FIG. 17A is an image of an exemplary lens for use with camera phones, according to some embodiments.

FIGS. 17B-17C are images of a bioassay device taken, respectively, with and without the lens of FIG. 17A, according to some embodiments.

DETAILED DESCRIPTION

Overview

Figure 1A:
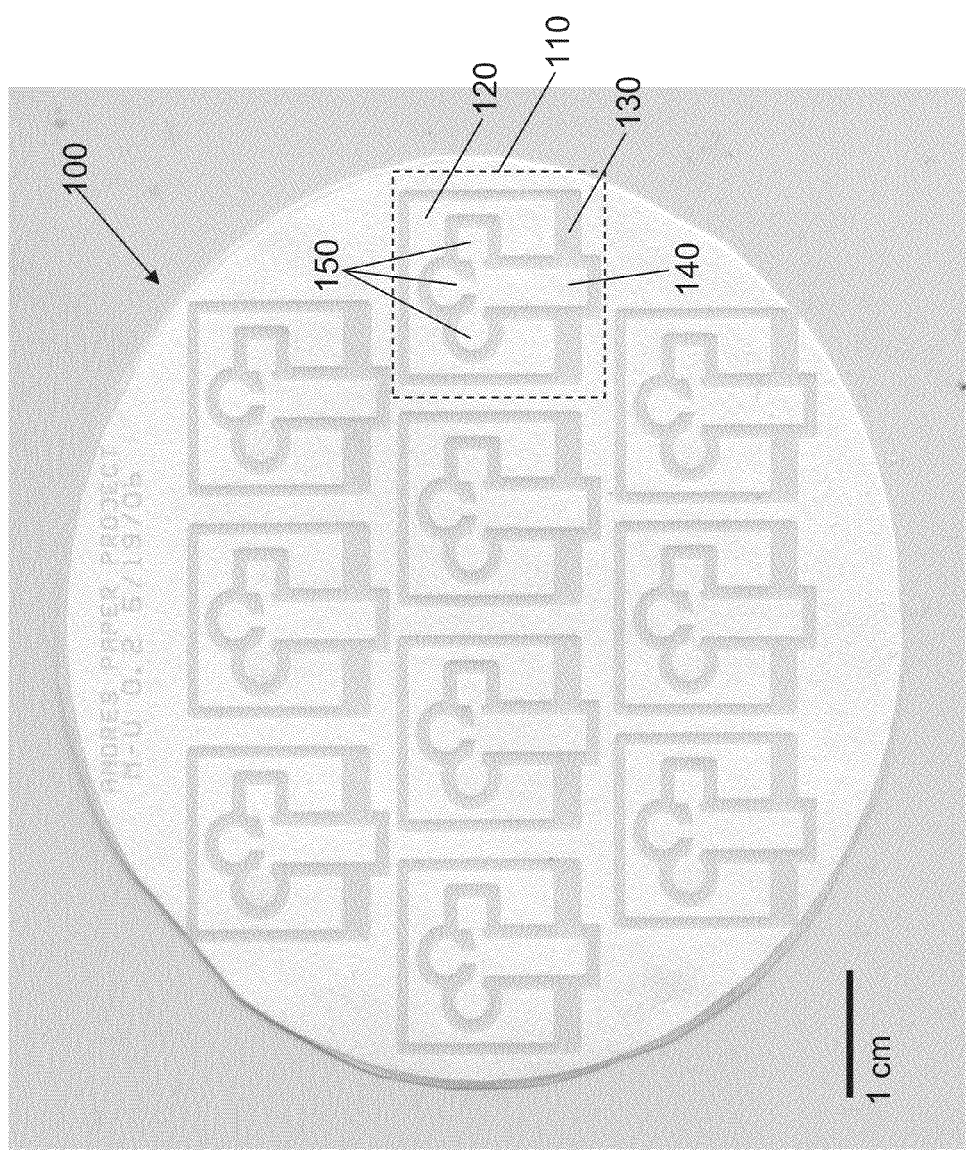
FIGS. 1A-1E are images of lateral flow bioassay devices, according to some embodiments.

Embodiments of the invention provide lateral flow and flow-through bioassay devices based on patterned porous media, methods of making same, and methods of using same.

Under some aspects, porous, hydrophilic media are patterned with hydrophobic barriers to provide a class of low-cost, portable, and technically simple platforms for running multiplexed bioassays on biological liquids. One example of a useful hydrophilic medium for bioassays is paper, which is inexpensive, readily commercially available, disposable, wicks liquids quickly, and does not need careful handling as do some conventional platforms. The paper or other porous, hydrophilic medium is patterned with hydrophobic barriers that provide spatial control of biological fluids and enable fluid transport due to capillary action within the regions the barriers define. The hydrophobic barriers can be polymeric, for example a curable polymer or a photoresist, and provide a substantially impermeable barrier throughout the thickness of the porous, hydrophilic medium within defined areas. Unlike conventional microfluidic devices that include empty fluidic channels or wells in polymer or glass, the regions bounded by these barriers are not empty, but instead are made from and contain the porous, hydrophilic medium.

In further contrast to conventional devices, some embodiments of the bioassay devices are made using photolithography by saturating the porous, hydrophilic medium with photoresist, exposing the saturated medium to a pre-determined pattern of light, and removing the photoresist based on the pattern, forming hydrophobic barriers made of photoresist. The pattern of the light can be selected to define assay regions, channel regions, sample deposition regions, and the like, the boundaries of which are at least partially defined by the hydrophobic barriers. Although photoresist is conventionally used with semiconductors, the inventors have discovered that, surprisingly, saturating a porous, hydrophilic medium with photoresist and performing photolithography on that photoresist allows for the fabrication of high quality features that are not available using conventional assay production techniques. Typical conventional assay production techniques involve applying a liquid to a porous medium in accordance with a pattern, and then hardening the liquid to form features. However, when the liquid is applied, it spreads laterally within the medium, thus causing a loss of definition in the features. Photolithography does not rely on applying liquid in accordance with a pattern, thus providing a significantly higher feature resolution than conventionally available. For example, significantly smaller features can be made using this photolithographic technique than can be made using screen-printing techniques, e.g., barriers having a thickness between about 1 mm and about 100 µm, e.g., between about 300 µm and 100 µm, or even smaller. Additionally, the technique can form features that do not vary significantly along their length, e.g., barriers having widths that vary by less than about 10%, by less than about 5%, or even less, along their length. Conversely, channels defined by such barriers will also have widths that do not vary significantly along their length, e.g., by less than about 10%, by less than about 5%, or even less, along their length. Other embodiments of the bioassay devices are based on other methods of production, such as soft lithography, which provide useful benefits and improved feature resolutions not available using conventional techniques for making assay devices, as described in greater detail below.

The bounded regions of the hydrophilic medium can be used to define one or more assay regions in a bioassay device. The assay regions of the bioassay device can be treated with reagents that respond to the presence of analytes in a biological fluid and which can serve as an indicator of analyte presence. Because many embodiments of the assays are intended to be easily usable without the use of complicated and expensive equipment, in some embodiments the device's response to the analyte is visible to the naked eye. For example, the hydrophilic medium can be treated in the assay region to provide a color indicator of the presence of the analyte. Indicators may include molecules that become colored in the presence of the analyte, change color in the presence of the analyte, or emit fluorescence, phosphorescence, or luminescence in the presence of the analyte. In other embodiments, radiological, magnetic, optical, and/or electrical measurements can be used to determine the presence of proteins, antibodies, or other analytes.

In some embodiments, to detect a specific protein, an assay region of the hydrophilic medium can be derivitized with reagents such as small molecules, that selectively bind to or interact with the protein. Or, for example, to detect a specific antibody, an assay region of the hydrophilic medium can be derivitized with reagents such as antigens, that selectively bind to or interact with that antibody. For example, reagents such as small molecules and/or proteins can be covalently linked to the hydrophilic medium using similar chemistry to that used to immobilize molecules on beads or glass slides, or using chemistry used for linking molecules to carbohydrates. In alternative embodiments, the reagents may be applied and/or immobilized by applying them from solution, and allowing the solvent to evaporate. The reagents can be immobilized by physical absorption onto the porous medium by other non-covalent interactions. In general, a wide variety of reagents can be used with the bioassay devices to detect analytes, and can be applied by a variety of suitable methods. These reagents could include antibodies, nucleic acids, aptamers, molecularly-imprinted polymers, chemical receptors, proteins, peptides, inorganic compounds, and organic small molecules. These reagents could be adsorbed to paper (non-covalently through non-specific interactions), or covalently (as either esters, amides, imines, ethers, or through carbon-carbon, carbon-nitrogen, carbon-oxygen, or oxygen-nitrogen bonds).

However, the interaction of some analytes with some reagents may not result in a visible color change, unless the analyte was previously labeled. The device can be additionally treated to add a stain or a labeled protein, antibody, nucleic acid, or other reagent that binds to the target analyte after it binds to the reagent in the assay region, and produces a visible color change. This can be done, for example, by providing the device with a separate area that already contains the stain, or labeled reagent, and includes a mechanism by which the stain or labeled reagent can be easily introduced to the target analyte after it binds to the reagent in the assay region. Or, for example, the device can be provided with a separate channel that can be used to flow the stain or labeled reagent from a different region of the paper into the target analyte after it binds to the reagent in the assay region. In one embodiment, this flow is initiated with a drop of water, or some other fluid. In another embodiment, the reagent and labeled reagent are applied at the same location in the device, e.g., in the assay region.

The bioassay devices can be in a lateral flow configuration, a flow-through configuration, a combination of the two, or in a 3-dimensional configuration. In a lateral flow bioassay device, liquid flows laterally through the device by capillary action, e.g., from a sample deposition region of the medium where sample can be introduced into the device, to an assay region of the medium, where the presence of analytes can be detected, via a channel defined by the hydrophobic barrier. Because the hydrophobic barrier defines the flow path of the liquid, appropriate selection of the barrier pattern can yield a multiplexed assay, in which the liquid flows from the sample deposition region of the medium to multiple assay regions via multiple channels defined by the barrier. The barrier can additionally be patterned such that the channels are sufficiently narrow to allow a relatively small volume of liquid (e.g., less than 10 µL) to flow to all of the desired regions of the device. Note however that the minimum feature size of the barrier is dependent to some extent on the selected fabrication technique, as described in greater detail below.

A flow-through bioassay device typically includes multiple layers, at least one of which is a porous, hydrophilic medium that is patterned with hydrophobic barriers. In use, liquid flows vertically from one layer to another, and the hydrophobic barriers constrain the lateral flow of liquid. One or more areas of the porous, hydrophilic medium can be treated to provide an assay for a target analyte, e.g., to provide a visible indicator (or other detectable indicator) of the presence of the analyte. In some embodiments, one layer of the device is treated with a stain or labeled reagent that provides a color indicator of the presence of the analyte, e.g., after the analyte interacts with a reagent in another layer. Note that some embodiments may include both lateral and flow-through of the liquid.

Under many aspects, a single drop of liquid, e.g., a drop of blood from a pinpricked finger, is sufficient to perform assays providing a simple yes/no answer to the presence of an analyte, or a semi-quantitative measurement of the amount of analyte that is present in the sample, e.g., by performing a visual or digital comparison of the intensity of the assay to a calibrated color chart. However, in order to obtain a quantitative measurement of an analyte in the liquid, a defined volume of fluid is typically deposited in the device. Thus, in some embodiments, a defined volume of fluid (or a volume that is sufficiently close to the defined volume to provide a reasonably accurate readout) can be obtained by patterning the paper to include a sample well that accepts a defined volume of fluid. For example, in the case of a whole blood sample, the subject's finger could be pinpricked, and then pressed against the sample well until the well was full, thus providing a satisfactory approximation of the defined volume.

Some embodiments further include equipment that can be used to image the bioassay device after deposition of the liquid in order to obtain information about the quantity of analyte(s) based on the intensity of a colorimetric response of the device. In some embodiments, the equipment is capable of establishing a communication link with off-site personnel, e.g., via cell phone communication channels, who perform the analysis based on images obtained by the equipment.

Under certain aspects, such bioassays can be fabricated using simple methods that generate patterned hydrophobic barriers in hydrophilic medium. For example, in some embodiments, the hydrophilic medium is soaked in photoresist, and photolithography is used to pattern the photoresist to form the barriers. Photolithography can be performed in the cleanroom, or, as demonstrated below, can also be performed outside a cleanroom, e.g., in a typical laboratory setting, without significantly impacting the quality of the fabricated barriers, and with significantly reduced cost. In other embodiments, micro-contact printing is used to define the barriers. Here, a "stamp" of defined pattern is "inked" with a polymer, and pressed onto and through the hydrophilic medium such that the polymer soaks through the medium, thus forming barriers of that defined pattern. Other fabrication techniques can also be used, some of which are described below. Depending on the intended application of the device and the specific barrier fabrication technique used, the barriers can have widths of greater than about 200 µm, and can define channels having widths on the order of microns, for example about 50 µm, or up to a several millimeters or larger.

While some embodiments include chromatographic paper as the porous, hydrophilic medium, in general any substrate that wicks fluids by capillary action and that is compatible with the selected patterning method may be used, e.g., nitrocellulose and cellulose acetate, cellulosic paper, filter paper, cloth, and porous polymer film. For example, nitrocellulose and cellulose acetate are commonly used and well-known membranes for use in fluid diagnostics, but are not compatible with solvents typically used in photolithography, so other methods would be more suitable for patterning them, as discussed in greater detail below. In addition, the hydrophilic medium and the hydrophobic barrier regions can be prepared using materials that are compatible with the testing conditions, e.g., temperature, pH, and/or ionic strength.

First, some embodiments of lateral flow bioassay devices and uses of same will be described. Then, some embodiments of flow-through bioassay devices and uses of same will be described. Then, some embodiments of methods for providing patterned hydrophobic barriers in porous, hydrophilic media will be described.

Lateral Flow Bioassay Devices

FIG. 1A is an image of an array 100 of lateral-flow bioassay devices having a hydrophilic medium and hydrophobic barriers, according to some embodiments of the invention. Each device 110 includes one or more patterned hydrophobic barriers 130, e.g., photolithographically patterned and cured photoresist, and porous medium 120, e.g., chromatographic paper. The hydrophobic barriers 130 define regions in the medium 120 that can be used to perform bioassays. In the illustrated embodiment, barrier 130 defines a sample deposition region 140, where a biological liquid can be deposited, and which also serves as a channel to wick fluid by capillary action, and a plurality of assay regions 150, into which the biological liquid flows. As described in greater detail below, assay regions 150 can be treated to provide assays for particular applications, e.g., to indicate the presence of sugar in urine. FIG. 1A illustrates ten individual devices 110 that were produced from a single 7.5 cm disk of chromatography paper; however the size of the paper and the number and type of devices can be selected appropriately for a given application.

Figure 1B:
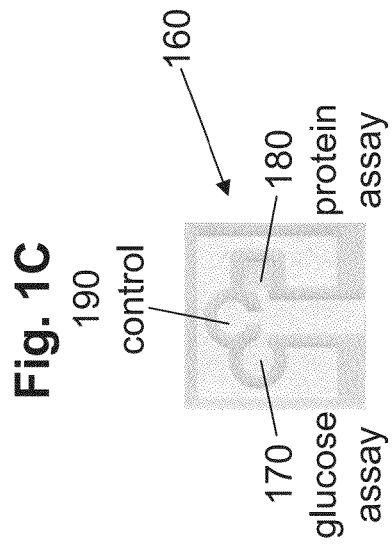

FIG. 1B is an image of one of the bioassay devices 110 of FIG. 1A, after absorbing about 5 µL of Waterman red ink by capillary action. The sample deposition region 140 absorbed the sample by capillary action, and the patterned hydrophobic barrier 130 directed the sample into the three assay regions 150. As the image shows, barrier 130 substantially restricts the sample flow within well-defined regions. Because the patterned regions of the device can be fabricated to a relatively small size, as described in greater detail below, only a relatively small volume of liquid (e.g., less than 10 µL is needed to sufficiently fill the regions 140, 150 defined by the barrier 130; in general, various configurations of devices may require about 0.1 µL to 100 µL of fluid to fill the device, depending on the size of the device and the sizes of the features within the device.

Figure 1C:
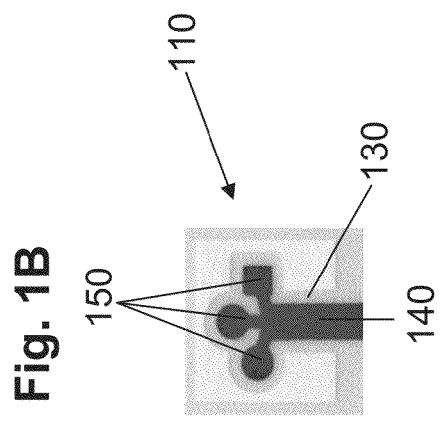

In some embodiments, one or more regions of the hydrophilic medium, e.g., paper, are derivatized for biological assays by adding appropriate reagents. FIG. 1C is an image of an embodiment of a bioassay device 160 in which assay regions 170 and 180 have been spotted with different reagents for diagnostic use, and a third assay region 190 is a control. In the illustrated embodiment, region 170 is prepared with a glucose assay that is adapted from that described in J. D. Peele, R. H. Gadsden, R. Crews, *Clin. Chem.* 1977, 23, 2242-2246, the entire contents of which are incorporated herein by reference. As described in greater detail below, the assay is prepared by spotting the assay region 170 with 0.3 µL of a 0.6 M potassium iodide followed by 0.3 µL of a 1:5 horseradish peroxidase/glucose oxidase solution (15 units of protein per mL of solution). When the assay is exposed to glucose, the glucose is oxidized by the glucose oxidase in the presence of water and oxygen, to give gluconic acid and hydrogen peroxide. The hydrogen peroxide is then reduced to water by the horseradish peroxidase with a concomitant oxidation of the iodide to iodine. The result is a visible color change from clear to brown that is associated with the presence of glucose.

Region 180 is prepared for a protein assay that is adapted from that described in M. J. Pugia, J. A. Lott, J. A. Profitt, T. K. Cast, *J. Clin. Lab. Anal.* 1999, 13, 180-187, the entire contents of which are incorporated herein by reference. As described in greater detail below, the assay is prepared by spotting the region 180 with 0.3 µL of a priming solution (0.3 µL) (92% water, 8% ethanol by volume, 2.5 g/L polyvinyl alcohol and 250 mM citrate buffer at pH 1.8), followed by 0.3 µL of a reagent solution (95% ethanol, 5% water by volume, 3.3 mM tetrabromophenol blue). The protein assay is based on the color change of tetrabromophenol blue (TBPB) when it ionizes and binds to proteins. A positive result in this case is indicated by a color change from yellow to blue.

Region 190 can be used as a control well and can be either spotted with iodide but no enzyme solution, or with enzyme solution but no iodide.

In this exemplary embodiment, the reagents were spotted with capillary tubes, however pipets, or pins such as used in microarrays could be used to mass-produce the assays. Ink-jet printing may also be used to deposit reagents. The spotted reagents were allowed to air dry at room temperature for at least 3 min before using the device.

Figure 1D:
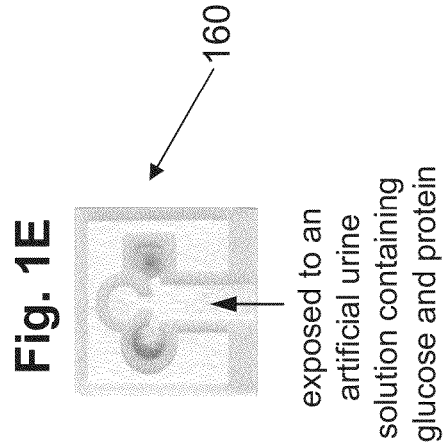

FIG. 1D is an image of the bioassay device of FIG. 1C after being exposed to 5 µL of an artificial urine solution that did not contain glucose or protein. Specifically, a 5 µL sample solution was transferred to a Petri dish with a micropipette, the bottom of the device was dipped into the solution, and the solution was absorbed into the paper by capillary action. The artificial urine solution was prepared according to the recipe provided by Brooks and Keevil (T. Brooks, C. W. Keevil, *Lett. Appl. Microbiol.* 1997, 24, 203-206, the entire contents of which are incorporated herein by reference). The artificial urine solution contained 1.1 mM lactic acid, 2.0 mM citric acid, 25 mM sodium bicarbonate, 170 mM urea, 2.5 mM calcium chloride, 90 mM sodium chloride, 2.0 mM magnesium sulfate, 10 mM sodium sulfate, 7.0 mM potassium dihydrogen phosphate, 7.0 mM dipotassium hydrogen phosphate, and 25 mM ammonium chloride all mixed in Millipore-purified water. The pH of the solution was adjusted to 6.0 by addition of 1.0 M hydrochloric acid. All reagents were obtained from Sigma-Aldrich.

Figure 1E:
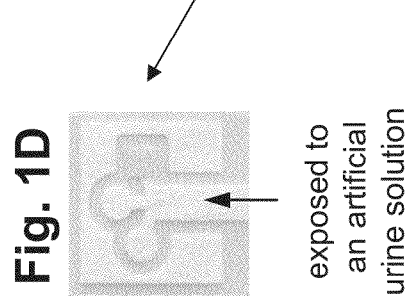

FIG. 1E is an image of the bioassay device of FIG. 1C after being exposed to 5 µL of the above-described artificial urine solution that additionally included 550 mM glucose and 75 µM bovine serum albumin (BSA). The control region 190 was spotted with the potassium iodide solution, but not with the enzyme solution. Both glucose assay region 170 and protein assay region 180 show a visible response to the presence of the respective analyte in the solution, while control region 190 does not show a significant response. A similar control containing the enzyme solution, but not the iodide, gave substantially the same results (data not shown).

The above-described tests were repeated under varying conditions of time and temperature in order to determine the stability of the assays. It was found that for this particular embodiment, the protein assay yielded comparable results irrespective of storage temperature and time, when stored wrapped in aluminum foil for about 15 days, either at about 0° C. or at about 23° C. The glucose assay appeared somewhat more sensitive to storage conditions, and showed decreased signal for assays performed about 24 hours after spotting the reagents when stored at 23° C.; however, when the glucose assay was stored at about 0° C. for about 30 days, it yielded comparable results as it did initially.

Figure 2:
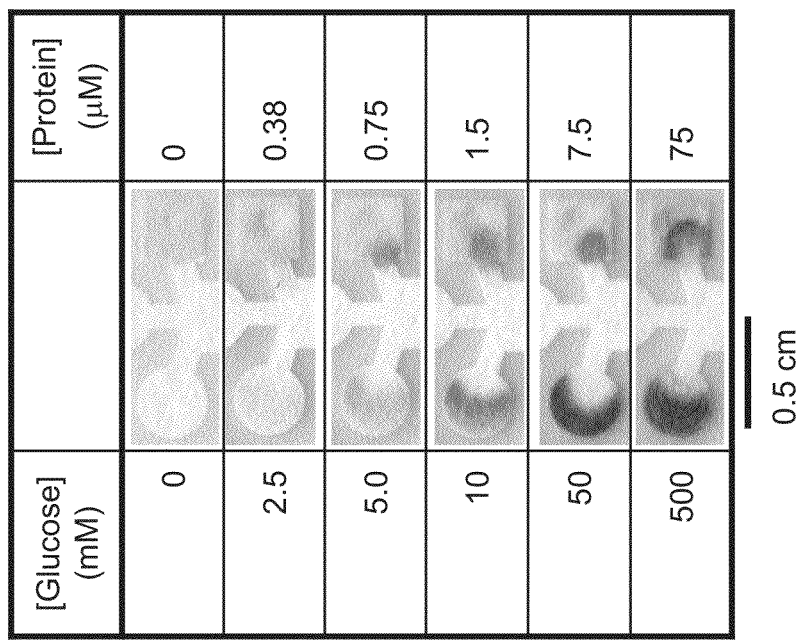
FIG. 2 shows images of lateral flow bioassay devices exposed to solutions containing varying concentrations of analytes, according to some embodiments.

FIG. 2 illustrates a sequence of tests performed on the exemplary bioassay illustrated in FIG. 1C. Specifically, the bioassay was exposed to samples of artificial urine containing glucose and protein in clinically relevant ranges (2.5-500 mM for glucose and 0.38-75 µM for BSA) by dipping the bottom of each device in 5 µL of the test solution. The fluid filled substantially the entire region defined by the patterned hydrophobic barrier within about one minute. The assays dried and the visible indicators substantially fully developed after approximately 10-11 min. The intensities of the resulting visible indicators approximately corresponded to the amount of glucose and protein in the test samples. In general, the lowest analyte concentrations that result in a detectable response, e.g., that result in a visible color change, define the lower limits of the assay sensitivity. In the tests performed here, color changes are visible at 2.5 mM of glucose and at 0.38 µM of BSA, indicating that the assays are at least this sensitive (and maybe lower). In comparison, typical commercially-available dipsticks detect as low as 5 mM glucose, or as low as 0.75 µM protein. Thus, the illustrative bioassay described above is at least as sensitive as these dipstick assays. Moreover, the assay format allows for the measurement of two or more analytes at once, whereas dipsticks are typically limited to measurement of a single analyte.

In general, by performing measurements with varying concentrations of analyte, a standard curve for the measurement may be determined. Thus, a given protein or antibody concentration can be correlated with a visible color change or intensity, allowing quantitative measurements. Note however that conventional radiological, optical and/or electrical measurements to determine the presence of proteins or antibodies are not incompatible with the platform, and in certain circumstances may be useful.

Figure 3A:
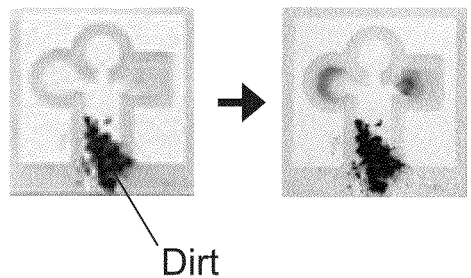
FIGS. 3A-3C depict lateral flow bioassay devices contaminated with dirt, plant pollen, and graphite powder, taken before and after exposure to solutions containing analytes, according to some embodiments.
Figure 3B:
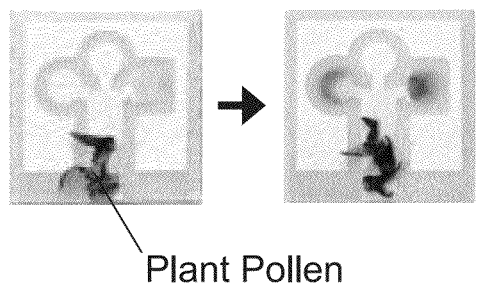
Figure 3C:
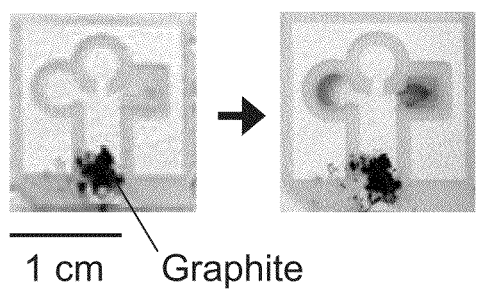

During typical use, liquid samples may not be measured under sterile conditions; for example, blowing dust or other particulate impurities may contact the liquid and/or the device. One useful feature of bioassays containing a porous, hydrophilic medium is that the medium also serves as a filter to remove at least some impurities that may be harmful to the biological sample. FIGS. 3A-3C are images of lateral flow devices as shown in FIG. 1C, that have additionally been contaminated with dirt, plant pollen, and graphite powder, respectively. These contaminants approximate conditions that can be encountered during the typical collection and analysis of samples in the field. After deposition of the contaminants, the devices were exposed to artificial urine samples containing 550 mM glucose and 75 µM BSA. As FIGS. 3A-3C illustrate, these particulates substantially do not move up the channels, and do not significantly interfere with the assay.

In general, there are at least two ways to introduce a liquid sample to a bioassay device, depending on the design of the particular embodiment. For example, some embodiments include a sample deposition area that is bounded by an edge of the porous, hydrophilic medium. The sample can be introduced to such a device by dipping this edge of the sample deposition area into the liquid. The liquid then flows laterally to one or more assay areas. Other embodiments include one or more sample deposition areas that are located centrally to the device, and have boundaries at least partially defined by the barriers, so that instead of dipping an edge of the device into a liquid, instead a drop of the liquid can be applied to the central sample deposition area(s). The liquid then flows laterally to one or more assay areas. Such a device can be used without the need for a separate, sterile sample repository, which not only reduces the burden on the patient to provide a relatively high-volume liquid sample within the repository, and also reduces the burden on health-care workers to handle and dispose of the liquid.

Figure 20:
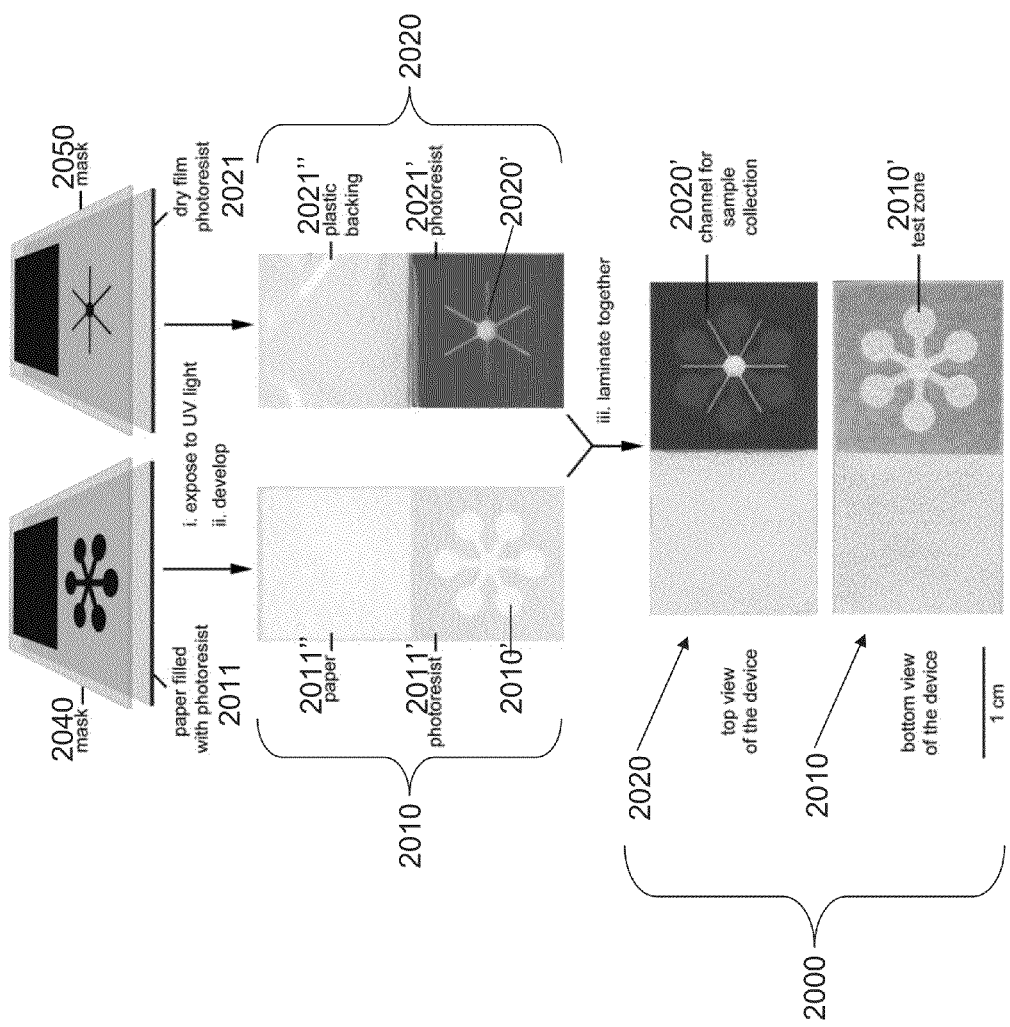
FIG. 20 illustrates plan and perspective views of layers in a lateral bioassay device, according to some embodiments.

FIG. 20 shows top and bottom plan views of an exemplary lateral flow bioassay device 2000. The device includes a top layer 2020 that is laminated to or otherwise bonded to a bottom layer 2010. As can be seen in the top view of the device, the top layer 2020 includes a substantially liquid-impermeable material, e.g., a dry-film photoresist, into which a channel 2020' is provided that can be used for sample collection. In the illustrated embodiment, the channel 2020' includes a central aperture and from which several narrow apertures radiate. The bottom layer 2010 includes a porous, hydrophilic medium, e.g., paper, and patterned hydrophobic barriers, e.g., patterned photoresist as described in greater detail herein, and which define a test zone 2010' that includes central sample absorption area from which several channels radiate and terminate in respective assay areas.

The device 2000 can be formed as illustrated in FIG. 20, according to some embodiments. First, to form the lower layer 2010, a porous, hydrophilic medium saturated with a hydrophobic material such as photoresist 2011 is provided, as described in greater detail below. The saturated medium 2011 is then exposed to UV or other suitable light through a mask 2040 that has a pattern selected according to the desired pattern of the hydrophobic barrier in the device 2000, and the hydrophobic material is then developed, as described in greater detail below, to form layer 2010. Layer 2010 includes a region 2011' that includes patterned hydrophobic barriers defining test zone 2010', and a paper tab 2011" that can be used for handling the device without contacting the test zone 2010'. The circular assay areas at the end of the channels of test zone 2010' can be treated as described in greater detail above and below to react with analytes.

Next, to form the upper layer 2020, a layer of hydrophobic material that is capable of patterning 2021, e.g., dry film photoresist, is provided. The material 2021 is then exposed to UV or other suitable light through a mask 2050 that has a pattern selected according to the desired pattern of the sample collection channel 2020', and the hydrophobic material is then developed, e.g., as described in greater detail below, to form layer 2020. Layer 2020 includes a region 2021' that includes sample collection channel 2020', and a region 2021" including plastic backing that can be used for handling the device without contacting the sample collection channel 2020'. Note that the upper and lower layers can be formed in any desired order or in parallel as desired.

The upper layer 2020 is then bonded to the lower layer 2010, e.g., by laminating them together, to form device 2000. The upper and lower layers are aligned such that region 2021" overlays region 2011" and region 2011' overlays region 2021'. In the illustrated embodiment, the central aperture of sample collection channel 2020' overlays the central sample absorption area of test zone 2010'. However, the narrow apertures radiating from the central aperture of sample collection channel 2020' do not overlay the channels or assay areas radiating from the central sample absorption area of test zone 2010'. Instead, the narrow apertures of channel 2020' are laterally offset from the channels and assay areas of test zone 2010', so that liquid substantially cannot flow directly from one of the narrow apertures of channel 2020' into one of the channels or assay areas of test zone 2010'. Instead, the narrow apertures of channel 2020' cause liquid to flow towards the central aperture of sample collection channel 2020', from which the liquid flows into the central sample absorption area of test zone 2010' and from there down the multiple channels and assay areas of test zone 2010.

In one example, lower layer 2010 was formed by saturating Whatman filter paper 1 with photoresist; baking the paper at about 95° C. for about 10 minutes; pressing the paper together with a mask (between two pieces of glass); exposing the paper to UV light through the mask; baking the paper at about 95° C. for about 10 minutes; soaking the paper in propylene glycol monomethyl ether acetate (PGMEA) for about 30 minutes to wash away unexposed photoresist; and washing the paper with propan-2-ol. The paper was then dried at about 25° C., and then plasma oxidized for about 10 seconds at about 500 torr to improve the hydrophilicity of the channels and test zones.

In the same example, lower layer 2020 was formed by first obtaining the dry film photoresist, which comes as a roll of light blue plastic protected on both sides by a clear plastic sheet (Riston®, from Dupont). The photoresist was pattered by exposing it to UV light through a mask (printed on a transparency); removing the plastic sheet from one side; and washing away unexposed photoresist with an aqueous solution of about 0.85 wt % $Na_2CO_3$. The patterned photoresist was then sprayed for about 1 second with 3M Spray Mount™ adhesive, aligned to the lower layer 2010 by hand, and the two layers were laminated together at about 100° C. An airbrush was used to apply an approximately 7 wt % solution of polyethylenimine (MW=20,000) in ethanol to the top of the device until the device appeared slightly wet. The coating was then dried by blowing on the device with a stream of nitrogen. The coating of polyethylenimine increased the hydrophilicity of the spokes in the dry film photoresist.

Figure 21:
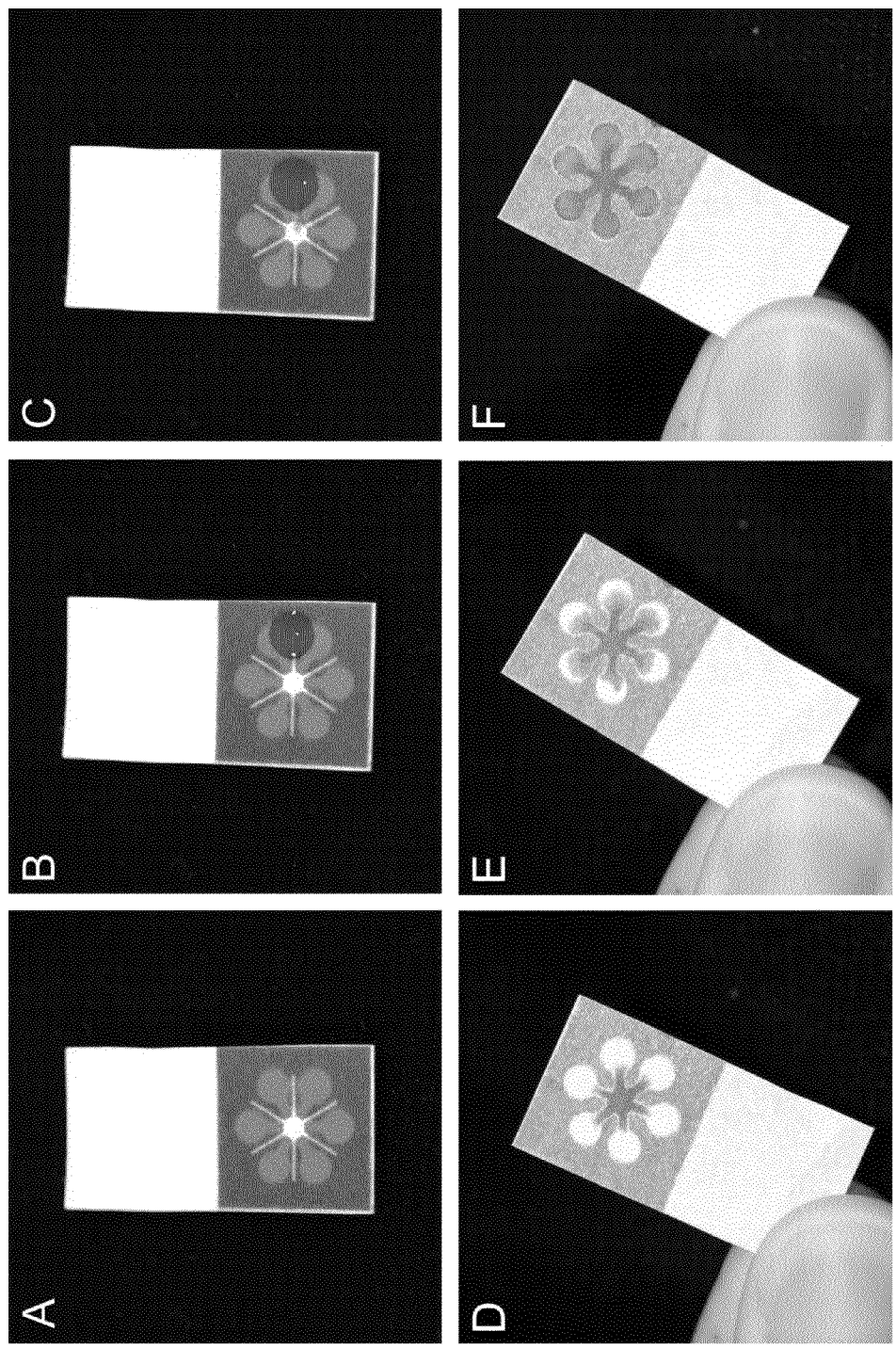
FIGS. 21A-21F are images of the lateral bioassay device of FIG. 20 at different times during exposure to a colored liquid, according to some embodiments.

FIGS. 21A-21F are images of a bioassay device fabricated using the example procedure described above, at different times during exposure to colored water. FIG. 21A is an image of the top side of the device before exposure to the water. FIG. 21B is an image of the top side of the device obtained immediately after depositing about 5 μL of the water on one of the narrow apertures in sample collection channel 2020' of upper layer 2020. FIG. 21C is an image of the top side of the device at a later time, and shows that the colored water travels along the narrow aperture upon which it is deposited, into the central aperture of sample collection channel 2020' and into the central sample absorption area of test zone 2010' of lower layer 2010.

FIGS. 21D-21F are sequential images of the bottom side of the device taken at different times after the colored water reaches the central sample absorption area of test zone 2010'. FIG. 21D shows the colored water after it has flowed from the central sample absorption area of test zone 2010' into the channels radiating from the central area. FIG. 21E shows the colored water after it has partially flowed from these channels into the assay regions. FIG. 21F shows the colored water after it has substantially completely filled the central sample absorption region, channels, and assay regions of test zone 2010'. In this embodiment, about 5 μL of water was sufficient to completely fill the test zone 2010'.

Because the porous media can be used to filter particles, they can also be used to perform diagnostics on whole blood samples. The presence of red blood cells typically complicates conventional diagnostics, for example requiring centrifugation or coagulation. In some embodiments the devices described herein, the porous medium can be selected so as to filter away the red blood cells, and allow free flow of the fluid components of the blood into the channel; alternately, the paper may be additionally treated to enhance binding to the red blood cells and prevent them from blocking the channel. In general, the porosity of the paper will determine the size of particles that may be transported through the paper. For example, proteins and small molecules can typically move readily through the paper, while particles on the order of the pore size can be filtered out.

While colorimetric tests are generally helpful in providing visual indicators of the presence or absence of analytes, lateral flow devices can also be used as a platform for quantitatively measuring the levels of analytes in biological liquids, e.g., urine. The ability to quantify multiple analytes simultaneously using inexpensive and portable bioassays can potentially be useful for identifying and monitoring disease in home health-care settings, in emergency situations, and in less-industrialized countries, as well as in laboratory and hospital settings.

In some embodiments, to obtain quantitative data, the bioassay device is imaged after exposure to liquid and after colorimetric results develop, e.g., using a desktop scanner, a portable scanner (such as a business card scanner), a digital camera, or a camera phone. Scanners are useful for recording the results of bioassays because they are relatively inexpensive, they have high resolution, the scanned image is typically in focus, and the intensity of the image is typically unaffected by lighting conditions. Digital cameras are portable and increasingly affordable, lightweight, and powerful, although the intensities of the recorded digital images may be affected by some lighting conditions, and the ability to focus the camera reproducibly may in some circumstances depend on the operator.

Camera phones typically have similar features as digital cameras, and also allow the recorded image can be transmitted electronically through existing communications infrastructure (e.g., cell phone channels) to an off-site laboratory, where the data can be analyzed by a specialist. The specialist can then return the results of the analysis (e.g., in real-time) to the person administering the test.

Some models of camera phones can focus automatically, and do not require an additional lens in order to sufficiently focus on an object, e.g., a bioassay, while some camera phones include cameras that cannot focus on objects that are too close to the camera. Some embodiments include a lens placed in front of the camera, which can enable the camera to take sufficiently focused images of objects relatively close to the camera. FIG. 17A is an image of an exemplary lens 1710 made from poly(dimethylsiloxane) (PDMS), which can be reversibly sealed to the lens on a camera phone. The lens 1710 was fabricated using a 10:1 mixture of PDMS base and curing agent (Sylgard® 184 silicone elastomer kit), and bubbles removed from the mixture by placing it under vacuum for 30 minutes. About 5 μL of PDMS was placed on the bottom of a Petri dish 1720, and cured upside down for 2 hours at 60° C. to create a concave PDMS lens. The PDMS lens 1710 was removed from the Petri dish 1720 with tweezers and placed over the lens of the camera phone. The camera phone was focused on the device by adjusting the distance between the camera phone to the device. In general, the focal length of the lens can be adjusted by changing the radius of curvature of the PDMS lens, e.g., by curing the PDMS on a surface that is either more or less hydrophilic than a Petri dish. A more hydrophilic surface will yield a lens with a larger radius of curvature, and a larger focal length. A less hydrophilic surface will yield a lens with a smaller radius of curvature. A lens with a smaller radius of curvature could also be obtained by curing the PDMS right side up, instead up upside down. Any converging lens (e.g. plan-convex lens, biconvex lens, Fresnel lens) with an appropriate focal length could be placed in front of the camera phone to focus the image.

FIG. 17B is an image 1730 obtained by placing the lens 1710 over the lens of a camera phone (Samsung Trace camera phone in automatic mode, 1.3 megapixels), and holding the camera phone about 4 cm above an exemplary bioassay device. FIG. 17C is an image 1740 of the same bioassay device taken with the same camera phone and the same distance from the device as in FIG. 17B. The image 1730 is significantly clearer than the image 1740, as a result of the PDMS lens.

In some embodiments, once results of an assay are converted to digital format, the intensity of the color developed in each test zone is measured using, e.g., Adobe® Photoshop® or another image analysis program. The intensity of the color is then compared with a calibration curve to calculate the concentration of the analyte.

Figure 4:
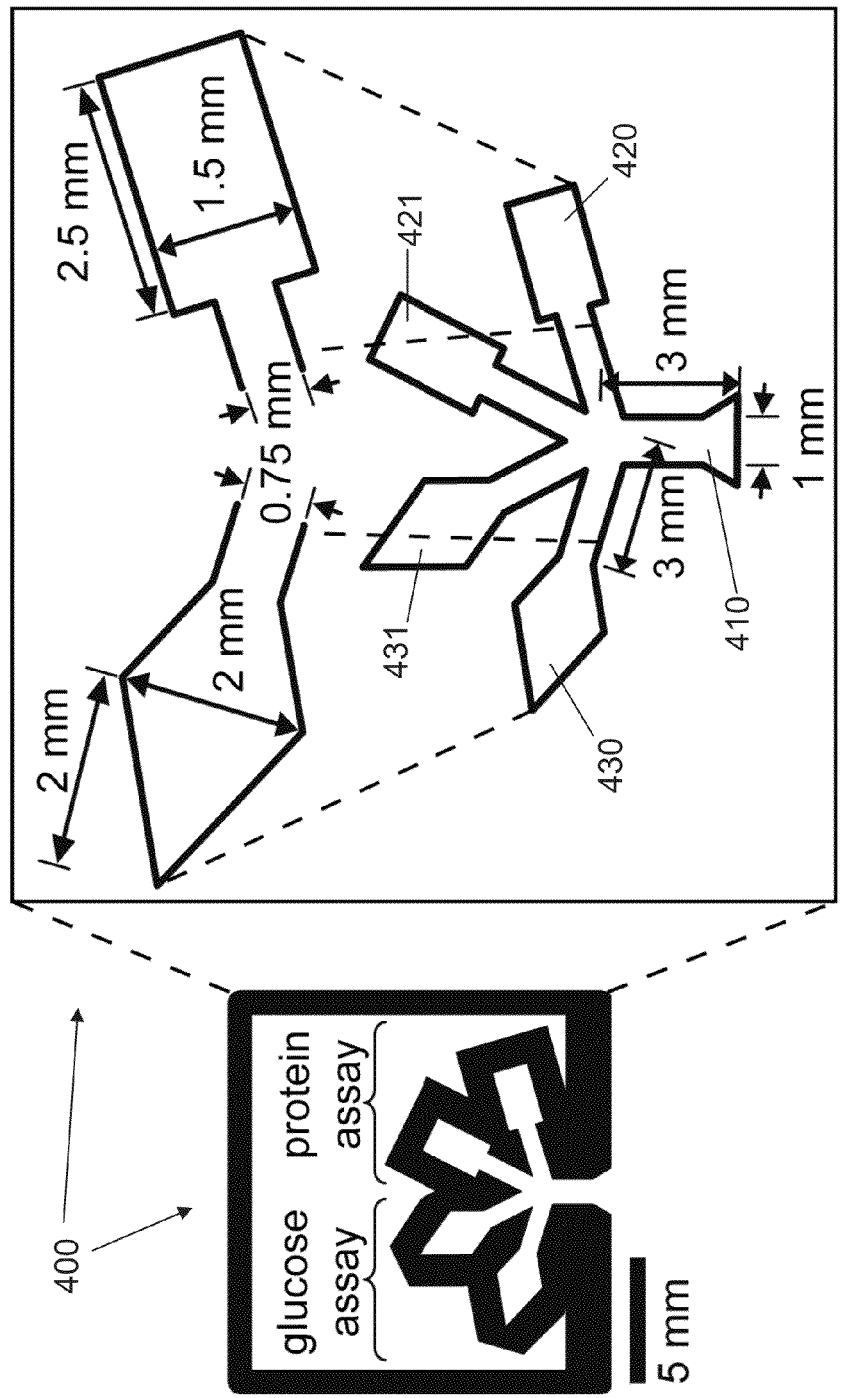
FIG. 4 schematically illustrates a plan view of a lateral flow bioassay device for use in measuring the presence of glucose and protein in biological liquids, according to some embodiments.

FIG. 4 schematically illustrates an exemplary bioassay device 400 that includes a central channel 410 that wicks a sample into the porous, hydrophilic medium (e.g., paper), and four side channels that direct the sample into four separate test areas 420, 421, 430, 431, each containing assay reagents. The design includes relatively narrow channels (about 0.75 mm wide) to reduce the volume of sample required for each assay. Generally, the larger the channel, the larger the volume of sample needed to run the assay. The test areas 420, 421 are treated with the protein assay described above, and the test areas 430, 431 are treated with the glucose assay described above.

Several features of this design make it suitable for use in home health-care or remote settings, for example. The approximately 3 mm long central channel 410 filters particulates from biological samples, similarly to the device described above, and the flared lower section of the central channel 410 facilitates absorption of the sample. The entire exemplary device can fit on a 1.6×1.6 cm piece of paper, so the device is not only small and portable, but also lightweight (~35 mg). The empty area above the test areas 420, 421, 430, 431 can be used for labeling and for manipulating the device.

In this illustrative example, there are also several design features specific to the particular glucose and protein assays used. Liquids cause the reagents for the glucose assay to move with the solvent front, while the liquids do not cause the reagents for the protein assay to move. The design of FIG. 4 includes two types of test zones to accommodate this differential behavior and to enhance the ability to quantify the assays. For the glucose assay, diamond-like shapes are provided in test areas 430, 431 to concentrate the reagents at the ends of the test areas. For the protein assay, rectangular-like shapes are provided in test areas 420, 421 to provide a defined region for relatively consistent analysis of the data. In general, four different bioassays could be performed with this exemplary design, but here two assays are provided in duplicate on each device. Additionally, in the embodiment of FIG. 4, the size of the channels and test zones were configured and designed to be large enough to be visible by eye, but at the same time small enough to limit the volume of fluid needed to run the assay to a tractable volume of sample (e.g., about 5 μL), such as a tear, or a drop of urine.

In general, the shapes and sizes of the channels and/or assay regions can be selected according to the type of liquid and/or analyte and/or detection method with which the device is to be used. For example, if the device response to the analyte is to be measured by imaging the device and analyzing the image with computer software, then the channels and assay regions need not necessarily be visible to the human eye so long as the imaging system can obtain a sufficient amount of information about the response to the analyte to perform an analysis. Or, as in the example above, if the reagent moves with the liquid applied to the device, then the assay regions can be shaped to capture and/or concentrate the reagent. Or, as in the example above, if the reagent is relatively stationary within the assay region, then the assay region can be shaped to provide an area which the image analysis software can easily analyze.

Figure 5:
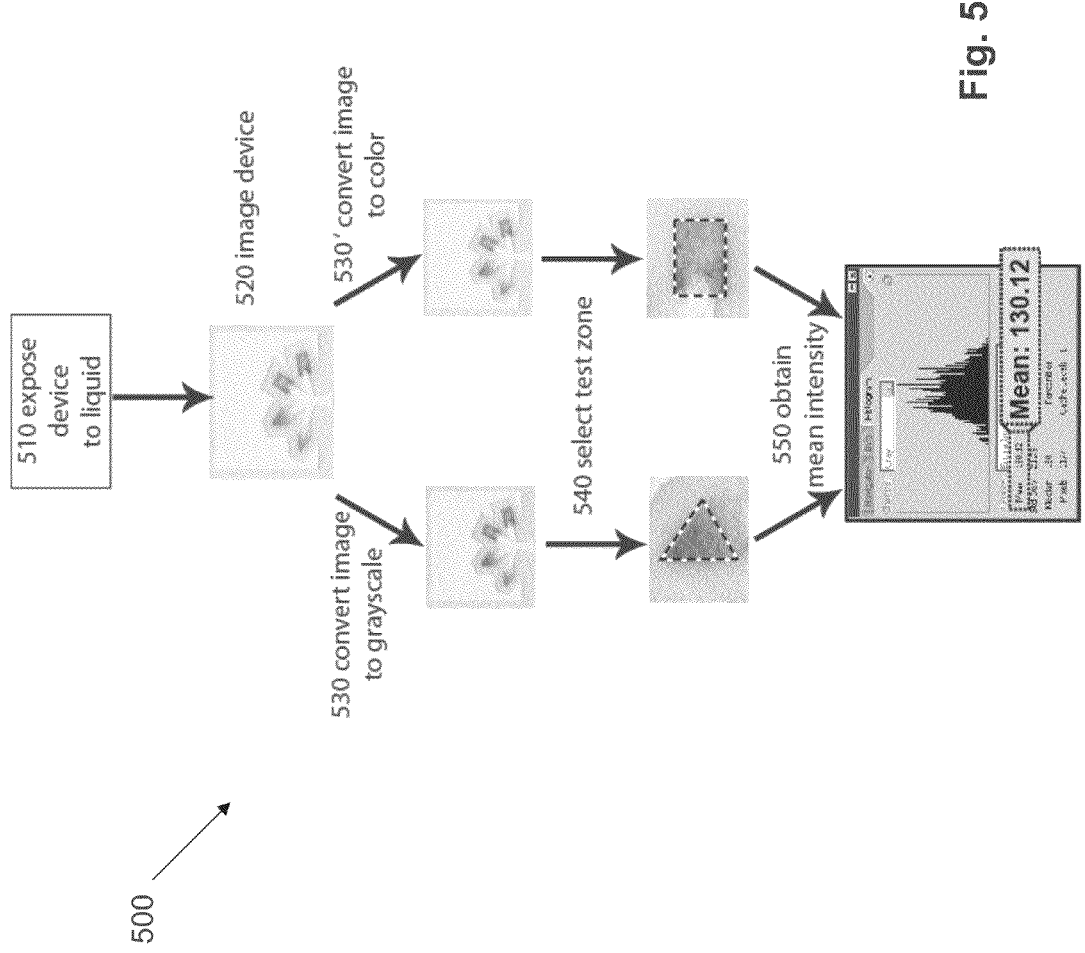
FIG. 5 illustrates steps for using a lateral flow bioassay device to quantitatively determining the presence of analytes, e.g., glucose and protein in a biological liquid, according to some embodiments.

FIG. 5 illustrates an exemplary procedure 500 for quantifying the levels of glucose and protein in urine. First, the bioassay device is exposed to the liquid 510, e.g., dipped into about 5.0 µL of an artificial urine sample solution with a known concentration of glucose and protein (bovine serum albumin, BSA). In one example, the solution and dipping procedure were the same as described above.

The exposed bioassay device is then imaged 520. In one example, thirty minutes after beginning the assay, the device was photographed using either a Nikon D50 digital SLR camera in manual mode with flash (6.1 Megapixels); a Sony Ericsson W660i camera phone in automatic mode with no flash (2.0 Megapixels with autofocus); or a Samsung Trace camera phone in automatic mode (1.3 Megapixels) with a PDMS lens. The device also was scanned using an Epson Perfection 1640SU scanner on default settings (color photo, 600 dpi); and a Docketport 465 sheetfed portable scanner on default settings (color, 600 dpi). These examples are nonlimiting, and other imaging devices can be used.

The image is then optionally converted to 8-bit grayscale 530 or converted to a color format such as CMYK 530', e.g., using Adobe® Photoshop®. Then, the test regions in the image are selected 540. In one example, the test regions were selected with the mouse using a rectangular marquee tool for the protein assay and a polygonal lasso tool for the glucose assay. For the protein assay, the entire test area was selected with a rectangle that was 2.5×1.5 mm wide. For the glucose assay, the triangle at the tip of the pattern was selected.

Next, the arithmetic mean of pixel intensity within each test area was used to quantify the colorimetric response 550. These mean intensities were subtracted from the mean intensities for devices with spotted reagents, but that were not exposed to the sample. Note that some or all of the analysis steps can be automated. For example, software running on the computer can be used to automatically select regions of the image to be subsequently analyzed. Or, for example, the entire analysis of the image can be automated, i.e., a computer program can automatically select the regions of the image, measure the mean pixel intensity, and convert the pixel intensity to a concentration using the equations derived from the concentration curves.

Figure 6:
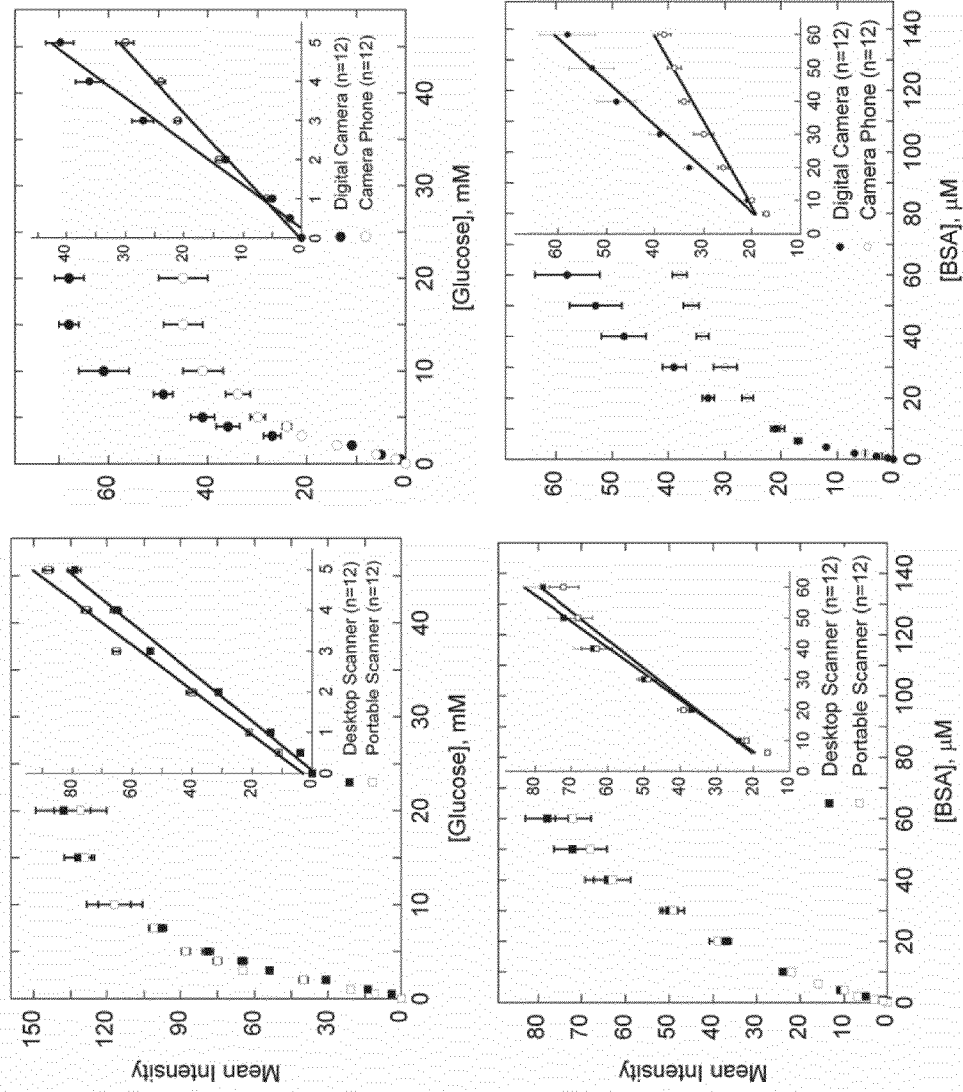
FIG. 6 illustrates the results of a quantitative determination of the presence of glucose and protein in biological liquids having varying concentrations of glucose and protein using a lateral flow bioassay device, according to some embodiments.

FIG. 6 illustrates signals obtained for different concentrations of glucose and protein in artificial urine according to some embodiments of the invention. Concentrations of glucose between 0 and 20 mM were measured. The protein assay was run using concentrations of BSA between 0 and 60 µM, and is shown in the graph at the bottom of the figure. The graphs contain data obtained using a desktop scanner (squares), a portable scanner (open squares), a digital camera (circles), and a camera phone with automatic focus (open circles); the inset shows the linear region of the data in greater detail. Each data point is the mean of twelve assays; error bars represent the relative standard deviations of these measurements. The linear region of the data was fit with a line; the slope (m), intercept (b), and $R^2$ value for each line are as follows: glucose (desktop scanner) (m=16.6, b=−1.54, $R^2$=0.991), glucose (portable scanner) (m=18.0, b=2.95, $R^2$=0.986), glucose (digital camera) (m=8.96, b=−2.12, $R^2$=0.983), glucose (camera phone) (m=6.17, b=0.186, $R^2$=0.986), protein (desktop scanner) (m=1.16, b=12.8, $R^2$=0.982), protein (portable scanner) (m=1.07, b=14.0, $R^2$=0.954), protein (digital camera) (m=0.771, b=14.5, $R^2$=0.980), protein (camera phone) (m=0.379, b=17.0, $R^2$=0.950).

As FIG. 6 illustrates, the signal obtained from the exemplary glucose and protein assays correlate approximately linearly with the concentration of analyte. The data points and error bars shown in this figure are the mean and standard deviation values, respectively, from at least twelve measurements per concentration of analyte. Linear least-squares fitting of each set of data gives coefficients of determination ($R^2$) of 0.95-0.99. The responses are approximately linear between 0 and 5 mM glucose and between 5 and 60 µM BSA, but deviate from linearity by leveling off at higher concentrations of analytes. The range of concentrations of glucose measured by using either the scanner or camera does not span the entire range of concentrations of glucose detected in urine clinically (1-56 mM). However, even levels of glucose in urine above 0.8 mM are indicative of disease, so it can be useful to detect low levels of glucose. The linear range of the glucose assay (0-5 mM) can allow for the quantitative measurement of low concentrations of glucose in urine. The linear range for the detection of protein is also appropriate for clinical use. The assay appears to be sufficiently sensitive to distinguish between glomerular disease ([protein]>35 µM), renal tubular diseases (10 µM<[protein]<20 µM) and microalbuminia (0.3 µM<[protein]<2 µM). Note that it may be possible to detect other concentrations of glucose and protein quantitatively by changing the concentrations of reagents or by shortening the central channel of the pattern to limit the distance between the test wells and the bottom of the device.

FIG. 6 also illustrates that the intensity of the signal was consistently smaller for the digital camera and camera phone than the desktop scanner and portable scanner with the particular lighting conditions, but the similarities between coefficients of determination and the consistent relationship between the slopes for the glucose and protein data suggests that high-quality digital cameras are nearly as effective as scanners for acquiring quantitative data. For example, calibration curves from the scanner and the camera were compared to quantify the levels of BSA and glucose in a test sample of artificial urine. A sample containing 4.5 mM glucose and 45 µM BSA was assayed twelve times, yielding results of 4.3±0.4 mM glucose and 46±5 µM BSA (using the scanner calibration curve) and 4.5±0.8 mM glucose and 48±6 mM BSA (using the camera calibration curve). Thus both techniques yield statistically comparable results.

In an exemplary procedure, because the data from the digital camera and camera phones is dependent to some extent on lighting conditions, each set of data was calibrated by running an artificial urine sample of known concentration. The intensity of signal for this known sample, was compared with the value expected from the curve shown in FIG. 6 to obtain a response factor that was used to adjust the experimental data to fit the calibration curve.

In general, image analysis protocols such as the exemplary protocol above can be used to analyze a variety of bioassay devices, and are not limited to the described embodiment. Any device that responds to the presence of an analyte in a way that can be digitally imaged can be analyzed using adaptations of the above-described procedure. For example, other designs of lateral bioassay devices, flow-through bioassay devices, and three-dimensional bioassay devices can also be analyzed.

As noted above, the performance of the bioassay devices are not significantly impacted by the presence of particulate contaminants. Table 1 shows results summarizing the quantitative analysis of exemplary artificial urine samples (4.5 mM glucose and 50 µM BSA) contaminated with either dirt, saw dust, or plant pollen. Each contaminant was measured six times using both the digital camera and the scanner; the digital signals were converted to concentrations using the calibration lines shown in FIG. 6. In each case, the contaminants had little effect on the concentrations of glucose (error ≤6%), and only plant pollen affected the concentration of protein (error ≤13%). This was a result from some protein from the flower that dissolved in the sample and caused an increased response.

TABLE 1

Quantitative results for assays using contaminated solutions of glucose (4.5 mM) and BSA (45 μM). The devices were scanned using the desktop scanner, and the concentrations were calculated using the calibration curves for the desktop scanner

| Contaminant | Glucose Observed Conc. (mM) | BSA Observed Conc. (μM) |
|---|---|---|
| Dirt | 4.4 ± 0.4 | 47 ± 9 |
| Sawdust | 4.3 ± 0.3 | 41 ± 5 |
| Pollen | 4.5 ± 0.6 | 86 ± 4[a] |

[a]About 34 ± 10 μM protein were independently measured in a 0 μM BSA sample contaminated with pollen.

As noted above, at least some control over the volume of sample that is analyzed is typically needed in order to make a quantitative measurement. However, in some environments, e.g., remote locations, a micro-pipette capable of dispensing 5 μl of sample may not available. Since the combined surface area of the channels and test zones on bioassay devices is constant in many embodiments, analytes may be obtained quantitatively by dipping the device into an unknown volume of sample, and by removing the device as soon as the sample had filled the test zones. Table 2 shows the results of measurements of three different concentrations of glucose and protein using a method in which approximately 20 μL of artificial urine was transferred to a Petri dish, the bottom of the device was dipped into the sample, and the device was removed from the sample as soon as the sample had filled the four test zones. The device was laid flat on a paper towel and after 30 min, the device was imaged as described above. The error in the measurements using this method are somewhat larger than those using fixed volumes of sample, but the levels of analytes can still be detected quantitatively.

TABLE 2

Quantitative detection of samples containing glucose (2.5, 3.5, and 4.5 mM) and protein (25, 35, and 45 μM). The values are the average and standard deviations of twelve measurements.

| | [Glucose], mM Known Concentration | | | [BSA], μM Known Concentration | | |
|---|---|---|---|---|---|---|
| Detection Method | 2.5 | 3.5 | 4.5 | 25 | 35 | 45 |
| | Observed Concentration | | | Observed Concentration | | |
| Desktop Scanner | 2.5 ± 0.4 | 3.5 ± 0.6 | 4.3 ± 0.4 | 27 ± 4 | 38 ± 6 | 46 ± 5 |
| Portable Scanner | 2.6 ± 0.5 | 3.4 ± 0.6 | 4.7 ± 0.4 | 28 ± 6 | 38 ± 5 | 45 ± 4 |
| Digital Camera | 2.4 ± 0.4 | 3.8 ± 0.5 | 4.5 ± 0.8 | 26 ± 6 | 37 ± 8 | 48 ± 6 |
| Camera Phone (with auto focus) | 2.3 ± 0.5 | 3.9 ± 0.7 | 4.5 ± 0.7 | 27 ± 7 | 36 ± 8 | 44 ± 7 |
| Camera Phone (with PDMS lens)[a] | 2.6 ± 0.6 | 3.2 ± 0.7 | 4.8 ± 0.5 | 26 ± 6 | 34 ± 8 | 45 ± 7 |

[a]The calibration curve from the camera phone with automatic focus was used to quantify these results.

The combination of patterned paper and a scanner or digital camera detector offers several advantages for quantitative detection of disease in home health-care settings or by first responders. This embodiment has been found to give accurate and quantitative results when detecting glucose and protein in urine (error ≤15%). These results also demonstrate that this inexpensive, simple, and portable paper-based technology is sufficiently quantitative in test systems that it can be useful in a medically relevant context.

Figure 7:
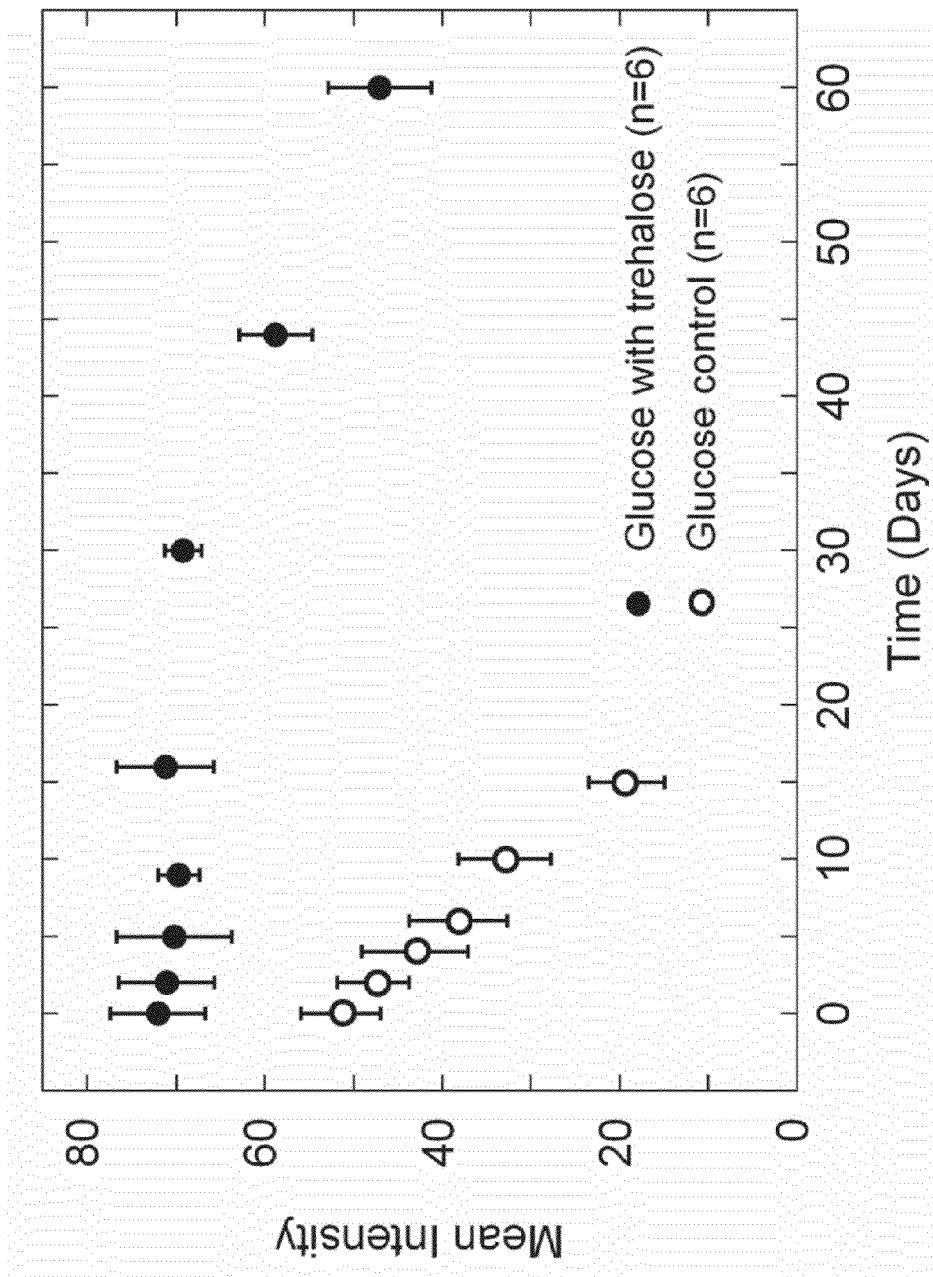
FIG. 7 illustrates the long-term stability of the flow device in the quantitative determination of the presence of glucose and protein in a biological liquid, with and without trehalose, according to some embodiments.

In some exemplary devices, the results for the glucose assay were observed to become less sensitive over time after spotting the reagents onto the device (when the device was stored at room temperature). An analytical device that would be useful in remote locations would desirably include reagents that remained stable for at least several days, and preferably for several weeks. In order to enhance the stability of the reagents for the glucose assay, trehalose, a disaccharide known for its ability to stabilize proteins in their active form in other applications, can be added. FIG. 7 illustrates that in some exemplary embodiments where trehalose was spotted onto paper (before the enzymes are added), no loss in enzymatic activity was observed over a period of two weeks (even when the devices are stored at room temperature), whereas in some exemplary embodiments prepared without trehalose, the glucose assay decreases linearly over time. Specifically, in the presence of trehalose, the intensity of signal for the glucose assay (when detecting 4.5 mM glucose in artificial urine) was approximately constant for about 30 days when devices were spotted with reagents and then stored at room temperature. The values on the graph are the average of six measurements, and the error bars represent the standard deviations from these averages. The protein assay can be stored at room temperature for over 2 months without loss of signal (data not shown). It will be appreciated that trehalose is not necessary to provide functional devices, and also that many other treatments can be used to enhance the stability of the assays.

Although the porous media of the above-described embodiments include different regions that are derivatized for detecting glucose and protein, in general the medium can be suitably derivatized for measuring many other analytes as well, and can be used in a variety of applications for which the availability of a simple, inexpensive test is useful.

For example, in some embodiments, the bioassay devices are used to perform urine analysis for infants, e.g., premature infants. Obtaining a sufficient amount of urine from an infant, particularly a premature infant, is difficult with conventional technology. The conventional technique is to put a cotton ball in the infant's diaper at the appropriate place, open the diaper 3 hours later, remove the cotton ball, and squeeze as much urine as possible (typically only fraction of a drop) onto an adult-sized urinalysis dipstick. This method results in a variety of problems, including that the specimen has typically at least partially evaporated, which affects the concentration of the analytes, as well as the specific gravity (and thus mobility) of the solution. Additionally, the analytes may have oxidized, which can affect the results of the protein, glucose, pH and/or other measurements.

In contrast, embodiments of the present invention provide devices that can be readily used to capture and analyze urine samples from infants, e.g., premature infants. In one embodiment, a lateral flow bioassay device, prepared for the desired assays, is positioned at a proper place in the diaper, and includes a paper channel that leads to the external surface of the diaper. When the infant urinates, urine flows through the device and the paper channel and displays external colorimetric indicators that can be read by a nurse, technician, or doctor. Such a device can be readily included in diapers because of its low cost. Moreover, reading the device does not require handling the infant, because the colors/assays occur on the outer surface of the diaper. This aspect can be particularly useful for premature infants, because handling can cause problems with their breathing, temperature, and/or stress levels, for example. Additionally, the result is available immediately after urination; this results both in a lack of need to wait to perform the test until a scheduled diaper change (typically every 3 hrs), and reduces the potential sample degradation that can occur with conventional assays. In some embodiments, the visual indicators are made particularly bright in order to indicate that the urine has been analyzed, so that the result can be quickly read.

A variety of assays can be incorporated into the diaper-based devices. For example, the glucose and/or protein tests described above can be included. In some embodiments, the vascular endothelial growth factor (VEGF) levels in the urine of infants, e.g., premature infants, can be monitored. VEGF levels are an indicator of the development of retinal disease. A conventional method of diagnosing retinal disease in premature infants is weekly or biweekly 15 minute examinations by an infant-retinal ophthalmologist, which is both expensive and disruptive to the infant. Detecting VEGF and other growth factors (such as IGF-1, or insulin-like growth factor 1) in urine can be useful for diagnosing retinopathy of prematurity, diabetes, cancer, and transplantation, as disclosed in S. K. Smith, Hum. Reprod. Update 1998, 4, 509-519, the entire contents of which are incorporated herein by reference. Detection of VEGF and other growth factors could be done in patterned-paper technology in the same way that pregnancy strip tests detect beta-HCG in the urine.

In other embodiments, the devices can be used to perform urine analysis of animals, e.g., laboratory animals, or pets taken to a veterinarian. Conventionally, animals are squeezed and/or tickled until they urinate; the urine is collected and then deposited onto adult human urinalysis dipsticks. In contrast, the lateral flow bioassays can be formed as relatively small paper "shreds" and scattered on the floor of the cage, on which the animal can urinate. Such colorimetric tests can be useful for measuring protein and glucose in lab animals where early diagnosis of diabetes or kidney disease is useful. In a veterinary setting, the determination of diabetes in obese cats and dogs is a useful test that can be difficult to do conventionally.

In other embodiments, the lateral flow bioassays can be used to analyze cerebrospinal fluid (CSF), for example to determine whether a patient has meningitis. Generally, diagnosis of meningitis includes a culture of CSF, a cell count to determine how many white blood cells are in the CSF, and measurement of the protein and glucose levels of the CSF. These three factors can be useful in determining the etiology of viral versus bacterial/parasitic/fungal meningitis. CSF is typically not available in large quantities (few mL), especially in children. Moreover, priority is given to the requirements of culturing CSF, leaving little or no sample for chemistry assays (glucose, protein). While conventional chemistry analyzers can perform glucose/protein measurements on specimens of a few μL, such tests are expensive and are typically unavailable in undeveloped countries. In contrast, the lateral-flow devices can inexpensively and rapidly provide a semi-quantitative readout of protein and glucose from CSF. For example, an application for resource-poor tropical settings could allow differentiation of cerebral malaria from viral meningitis by screening protein and glucose levels in the CSF. These disorders require drastically different treatments, and proper differentiation could spare patients from unnecessary medications and their not-inconsequential side effects.

In some embodiments, the devices can be used for breast milk analysis, e.g., to determine protein, fat, and glucose levels in the breast milk, which can help breast-feeding mothers adjust their feeds/pumpings to capture adequate calories. This issue is particularly important to prematurely born babies, where nutrition is critical to catch-up growth.

In other embodiments, the devices can be used in tissue engineering applications, for example in the generation of small "tissues" of liver, pancreas, islet cells, and other exocrine/endocrine organs for the purposes of replacement therapy. Monitoring the output of these small numbers of cells, e.g., measuring albumin output from small cultures of hepatocytes, can be difficult. Catalytic chemistries, such as ELISA, can be incorporated into the devices in order to make measurements of relatively small specimens. ELISA-type assays can be in the form of lateral flow or flow-through devices, where enzyme-labeled antibodies, for example, can be deposited into a region on the device, and then solvated by the biological fluid as it wicks through a device. The labeled antibody can bind to an antigen in the sample, and this complex further bind to an antibody that is attached (covalently) or adhered (non-covalently) to the substrate. Substrates for the enzyme attached to the antibody could be provided through a separate channel in the device, or by manual addition of reagents after the biological fluid has passed through the device.

In still other embodiments, the devices can be used in ophthalmology, e.g., in analyzing components in the vitreous fluid (the contents of the eye) or in tear films. Such analysis can be useful in diagnosing a variety of conditions (e.g., infections, tumors, trauma, response to systemic inflammation like rheumatoid arthritis). Eye fluids can be quickly analyzed, e.g., to determine the levels of antibodies and/or cytokines.

In other embodiments, the devices can be used to measure components in broncheoalveolar lavage fluid to diagnose, e.g., aspiration from gastroesophageal reflux of stomach contents.

In general, the devices are suitable for detecting biochemical markers of metabolism, stress, and disease in plants, animals, and humans. The devices also can be used to detect pollution and other analytes in water and soil, and are suitable for detecting analytes in other fluids like: cosmetics, oils, fuels, and others.

Flow-Through Bioassay Devices

While some embodiments generally operate by lateral flow of the liquid sample in the porous medium in channels defined by the hydrophobic barriers, in some embodiments the sample flows through multiple layers of hydrophilic media, i.e., in a "flow-through" configuration. In flow-through devices, hydrophobic barriers laterally contain the liquid as it flows transversely from one layer into another. The different layers of porous media can be treated, or left untreated, as appropriate for a given application.

Figure 8A:
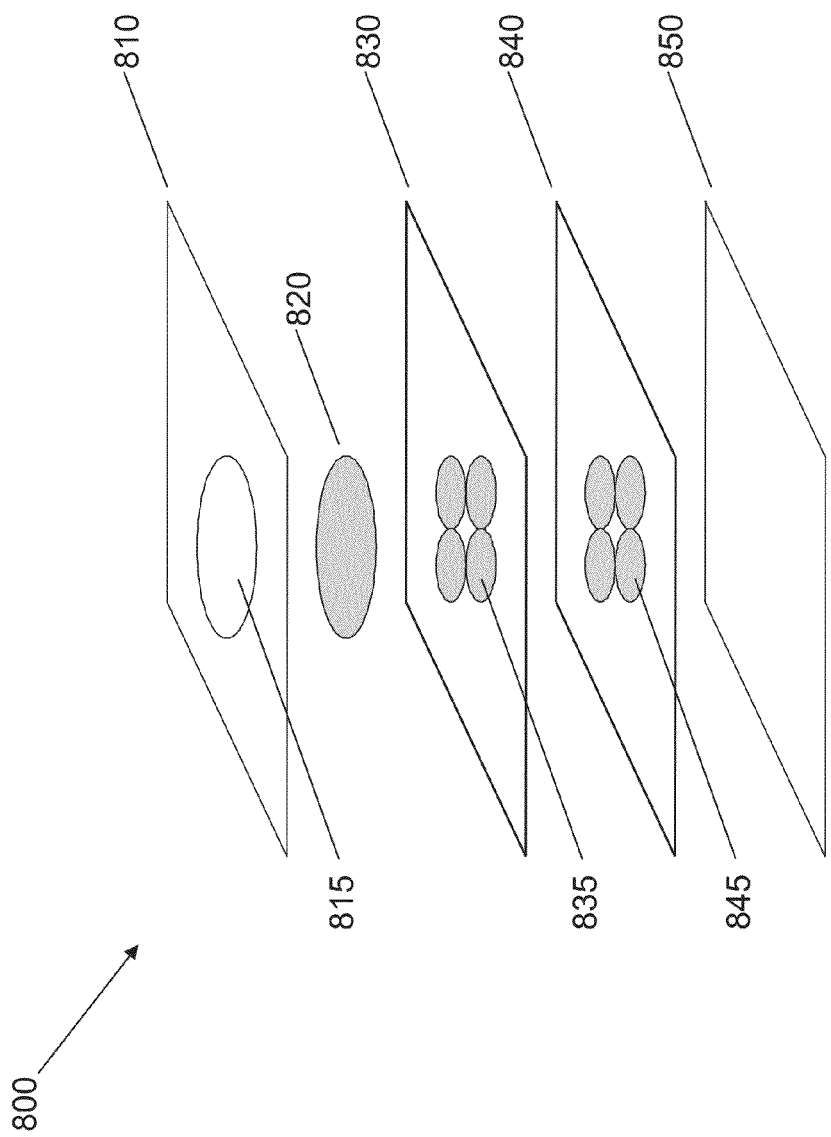

FIG. 8A is a schematic illustration, in perspective view, of a flow-through device 800 according to some embodiments of the invention. The device includes upper and lower protective coatings 810, 850, an optional filter 820, and porous media 830, 840. Upper and lower protective coatings 810, 850 hold the other layers of the device adjacent to one another, provide the device with additional strength and stability, reduce evaporation from the device, and protect the other layers from external contamination. Upper protective coating 810 includes an aperture 815 through which a liquid sample can be deposited onto the lower layers. Upper and lower protective layers can be, e.g., polymer coatings. One example of a useful protective coating is commercially available adhesive tape, which is inexpensive and which will readily bind the surfaces of layers that it contacts. Laminates are also useful.

Filter 820, e.g., glass fiber filter or other commercially available filter, can optionally be included when it is likely that filtering the sample will be necessary, for example if the presence of dust or other contaminants are expected, or if the device will be used with whole blood samples and removal of red blood cells is desired. Porous medium 830, e.g., cellulosic paper, includes one or more patterned hydrophobic barriers that define regions 835 in which reagents can be spotted or otherwise applied. Porous medium 840, e.g., cellulosic paper, likewise includes one or more hydrophobic barriers that define regions 845 in which other reagents can be spotted or otherwise applied. In some embodiments, the reagents in regions 835 react with an analyte in a sample to produce an intermediate reagent. These intermediate reagents pass with the excess fluid into regions 845, where they react with a second set of reagents previously absorbed into region 845. In some embodiments, this second reaction gives a colorful product. The layered structure inhibits contact between reagents in regions 835 and 845 until the analyte is present.

FIG. 8B is a schematic illustration, in perspective view, of a flow-through device 800' according to some embodiments of the invention. The device is similar to the device shown in FIG. 8A, and includes upper and lower protective coatings 810', 850', an optional filter 820', and porous media 830', 840' which can be substantially the same as those described above. The device 800' further includes an absorbent medium 860' that acts as a pump to draw liquid through layers 820', 830', and 840' of the device. In some embodiments, the reagents in regions 835' are antigens, which can be used to detect antibodies in a biological sample. In other embodiments, the reagents are antibodies for detecting antigens; in further embodiments they are nucleic acids, aptamers, molecularly-imprinted polymers, or other chemical receptors formulated to bind antigens, e.g., nucleic acids, proteins, small organic molecules, or inorganic ions. The reagents in region 845' can be adhered to layer 840', either covalently (e.g., using chemistry described previously) or non-covalently (e.g., through non-specific adsorption).

An exemplary assay performed using device 800' involves addition of a biological fluid to filter 820'; the fluid is distributed into the filter and excess fluid passes through the filter and is distributed into regions of layer 830'. Excess fluid dissolves reagents, e.g., labeled secondary antibodies, that were deposited into layer 830', and carries them to layer 840'. The analyte in the fluid, e.g., an antibody, binds to the receptors attached to regions 845', and the labeled reagents from regions 835' bind to the analyte. Excess fluid and reagents are carried into layer 860', which is hydrophilic and serves as a region for collecting excess fluid and reagents. Optionally, a drop of water, buffer, or other wash fluid can be added to filter 820' to wash excess reagents through the device into layer 860'; this washing step can remove non-specifically bound labels and reduce background signal. This device is suitable for, e.g., immunoassays, of which one assay may be, but is not limited to, an ELISA assay. An exemplary ELISA assay would include an enzyme-labeled secondary antibody, e.g., labeled with horseradish peroxidase, in region 835'. Addition of reagent, e.g., iodide, to region 845' after completion of an assay can lead to amplification of the signal for the assay, e.g., by horseradish peroxidase catalyzing the conversion of iodide to iodine, giving a brown color.

Note that not all of the layers need be included in all embodiments. For example, in some embodiments only a single layer of porous medium, e.g., medium 830 in FIG. 8A, is needed to perform a bioassay on a sample of interest. Other embodiments may include more or different layers than those illustrated in FIGS. 8A and 8B. Also, multiple devices can be provided in a given unit (e.g., on a single piece of porous medium) which can readily allow multiple diagnostic tests to be run in parallel or in sequence. As described in greater detail below, each of the devices may itself be multiplexed, thus allowing many different kinds of measurements to be performed at once.

FIGS. 9A and 9B illustrate front and back views, respectively, of an exemplary vertical-flow device 900 according to some embodiments. As can be seen in FIG. 9A, the device includes protective upper layer 910, e.g., adhesive tape, filter 920, and porous medium 930, e.g., filter paper. The protective upper layer 910 includes an aperture similar to that shown in FIG. 8A, which provides an area where the liquid sample can be deposited onto filter 920, e.g., glass fiber filter. Protective upper layer 910 also optionally includes a "tab" that extends past the edge of porous medium 930, and allows for easy handling of the device. Porous medium 930 includes a hydrophobic barrier that defines regions (not visible in this image) through which the sample can flow after being applied to filter 920.

FIG. 9B shows a back view of device 900. The device includes protective lower layer 950 and regions 935 for sample analysis, which are defined by the hydrophobic barrier in porous medium 930. In the illustrated embodiment, there are four regions 935 that are each treated to provide a different assay; however in general other shapes and numbers of regions, and other configurations are possible. In contrast to the lateral flow devices described above, here the assay regions are separated from one another by the hydrophobic barrier. However, some embodiments include assay regions that are in fluidic communication with each other. Such embodiments may operate as combination lateral and flow-through devices.

Figure 10:
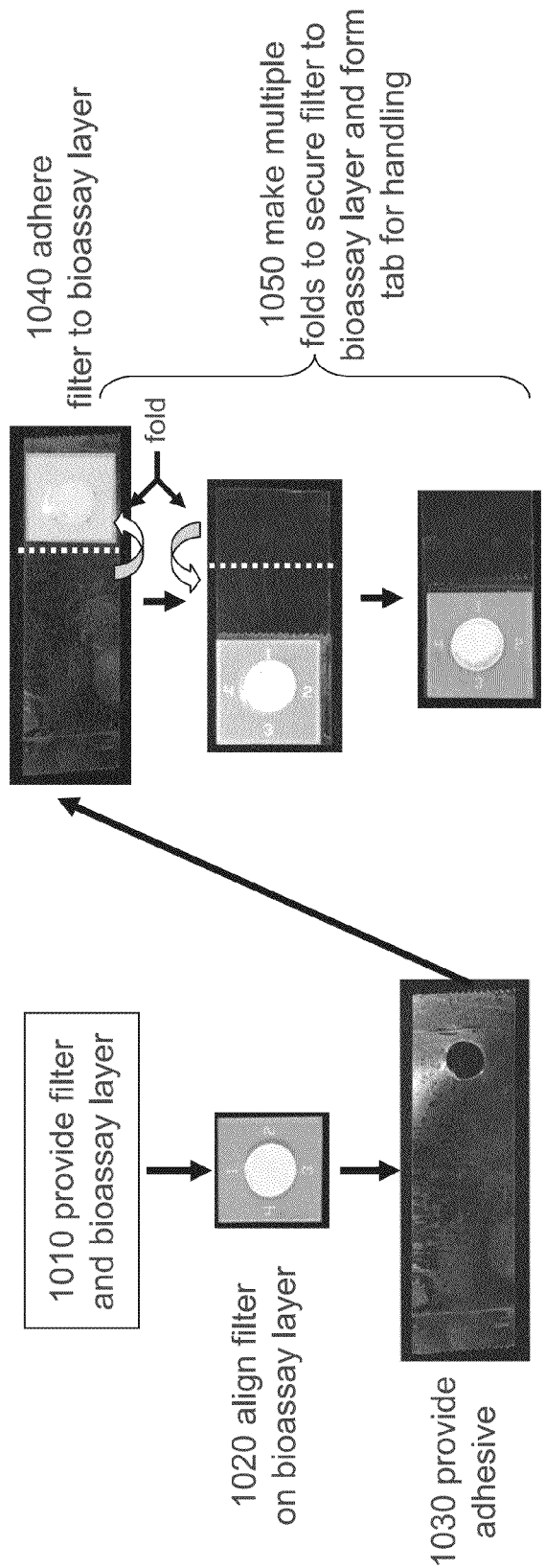
FIG. 10 illustrates an exemplary method for assembling a flow-through bioassay device, according to some embodiments.

FIG. 10 illustrates an exemplary procedure for assembling the lateral flow device of FIGS. 9A-9B. First, the bioassay layer and filter are prepared 1010. In one example, the bioassay layer is a porous medium having patterned barriers and assays spotted in regions defined by the barriers, e.g., as described above, and the filter is a 9-mm diameter piece of glass fiber filter paper (Whatman GF/C) prepared using a hole punch. The filter is aligned over the bioassay layer 1020. The protective layer, e.g., adhesive, is provided 1030. In one example, a 7-mm diameter hole is punched out of clear adhesive tape (e.g., Scotch tape)) (7×1.9 cm) ~7 mm from one end of the tape. The filter is then adhered to the bioassay layer 1040 using the adhesive. The adhesive is then folded a series of times 1050 to secure the filter to the bioassay layer, with the hole in the adhesive placed over the glass fiber filter, and the excess length of the tape wrapped around the bioassay layer to seal the device.

In one example, the device as fabricated is relatively lightweight (about 50 mg) and small (about 36×18×0.3 mm), but is large enough to be manipulated by hand. The device was designed to perform four assays that yield indicators of liver function, by treating the four regions 935 with different assays.

A first region 935 of the fabricated device was treated to detect alanine aminotransferase (ALT) using a method modified from the procedure reported in U.S. Pat. No. 5,279,944, the entire contents of which are incorporated herein by reference. The assay relies on the formation of pyruvic acid (catalyzed by ALT) in the presence L-alanine and alpha-ketoglutaric acid. The pyruvic acid subsequently reacts with pyruvic oxidase to produce hydrogen peroxide. The hydrogen peroxide reacts with horseradish peroxidase in the presence of 4-aminoantipyrine and sodium dimethylaminobenozoic acid to give the 4-N (1-imino-3-carboxy-5-N,N dimethylamino-1,2-cycloexandion) antipyrine sodium salt; the assay turns a red/purple color when ALT is present.

An ALT assay on paper is prepared, in one exemplary embodiment, by spotting the following solutions into the assay well in the order listed, followed by 10 min of drying between each solution: 1) A 0.3 µL of a 0.3 M trehalose solution in Millipore water; 2) A 0.3 µL solution containing L-alanine (1 M), α-ketoglutaric acid (30 mM), $KH_2PO_4$ (2 mM), $MgCl_2.6H_2O$ (20 mM), and thiamine pyrophosphate (TPP) (2 mM) in 200 mM Tris-HCl buffer (pH 7.35); 3) A 0.3 µL solution containing 4-aminoantipyrine (2 mM) and sodium dimethylaminobenozoic acid (10 mM) in 200 mM Tris-HCl buffer (pH 7.35); and 4) A 0.3 µL solution containing pyruvic oxidase (6 U/ml) and horseradish peroxidase (6 U/ml) in 200 mM Tris-HCl buffer (pH 7.35). The calibration curves for ALT were prepared by spotting 0.5 µL solutions of ALT in 50 mM sodium phosphate buffer (pH 8.0) containing 150 mM NaCl into the test areas.

A second region 935 of the fabricated device was treated to detect levels of proteins in plasma using a procedure modified from that reported in *J. Clin. Lab. Anal.* 1999, 13, 180 and in *Angew. Chem. Int. Ed.* 2007, 46, 1318. Specifically, 0.3 µL of a 250-mM citrate buffer solution (pH 1.8) was spotted in the test area, followed by 10 min of drying, and then 0.3 µL of a 4.5-mM tetrabromophenol blue (TBPB) solution in ethanol was added; the paper was dried again for 10 min. The calibration curves were prepared by spotting 0.5 µL solutions of BSA (ranging in concentration from 0.1-2 mM) in 50 mM sodium phosphate buffer (pH 8.0) containing 150 mM NaCl into the test areas.

A third region 935 of the fabricated device was treated to detect levels of alkaline phosphatase (ALP) in plasma were measured using an assay modified from that described in "Rapid and Sensitive Colorimetric Method for Visualizing Biotin-Labeled DNA Probes Hybridized to DNA or RNA Immobilized on Nitrocellulose: Bio-Blots," Leary, J. J.; Brigati, D. J.; Ward, D. C., *PNAS*, Vol. 80, No. 13, 1983, pp. 4045-4049, the entire contents of which are incorporated herein by reference. Specifically, 0.3 µL of 500 mM Tris buffer (pH 9.5) was spotted into a paper test area, the area allowed to dry for 10 min, then 0.3 µL of 2.5% nitro blue tetrazolium in 70% dimethylformamide was spotted, followed by 10 min of drying and 0.3 µL of 5% 5-bromo-4-chloro-3-indolyl phosphate in 100% DMF. The test area was allowed to dry for 30 min. The calibration curves were prepared by spotting 0.5 µL solutions of alkaline phosphatase in 500 mM Tris buffer (pH 9.5) into the test areas.

A fourth region 935 of the fabricated device was treated to detect levels of aspartate aminotransferase (AST) in plasma, using a procedure modified from that reported in U.S. Pat. No. 5,834,226, the entire contents of which are incorporated herein by reference. Specifically, after the back of the test substrate was covered in tape to minimize evaporation, 2.0 µL of a 5% w/v trehalose solution in Millipore water was spotted into the test areas. After drying for 10 min, 2.0 µL of a solution containing 1.0 M L-cysteinesulfinic acid and 0.1 M mono sodium 2-ketoglutarate in 200 mM TRIS buffer (pH 8.0) containing 0.0237 M NaCl, and 4.5 mM EDTA disodium salt, was spotted into the test areas. After drying another 10 min, 2.0 µL of a dye solution (containing 0.25 g polyvinylalcohol, 7.5 mg methyl green, 7.5 mg rhodamine B, 2.8 mg $ZnCl_2$ in 25.0 mL of deionized water) and 0.06% Triton X-100 was spotted into the test areas. The calibration curves were prepared by spotting 2.0 µL solutions of aspartate aminotransferase (in concentrations ranging from 0.05 U/mL to 2.50 U/mL) in 50 mM sodium phosphate buffer (pH 8.0) containing 150 mM NaCl into the test areas.

In some embodiments, the device is exposed to a drop of blood that is obtained by piercing a finger using a lancet, where the blood is added to the device by holding the device between the pierced finger and the thumb (so that the drop of blood is aligned on the filter). The device is held without pressure for about 60 seconds, then squeezed gently for about 10 seconds. After about 70 seconds the device no longer needs to be held; the results of the assays, however, are not analyzed until after 30 min. The results of the assays are observed by peeling away the protective casing (i.e., the tape) from the patterned paper (this process also removes the glass fiber filter). The results of the assays can be visualized qualitatively by comparison with color charts, or they can be quantified by digitizing and analyzing the results, e.g., as described in greater detail above.

Because any desired pattern can be defined in the porous medium, a wide range of applications beyond bioassays may be envisioned. For example, the porous medium, e.g., paper, can be patterned into channels, and electrophoresis subsequently performed on samples in those channels by applying an electric field. Although the use of paper in electrophoresis is well known and understood, the path length of the sample, and thus the degree of separation between charged particles in the sample, has conventionally been limited to the length of the paper used. Here, because the paper can be arbitrarily patterned, channels can be fabricated with a "zig-zag" or other pattern that increases the path length of the channel relative to the length of the paper. Moreover, patterning allows the channels to be significantly narrower than in conventionally paper-based electrophoresis, so much smaller sample sizes can be used.

In some embodiments, layers of patterned porous, hydrophilic media (e.g., paper) and layers of insulating material (e.g., double sided tape) are stacked in alternate order to produce three dimensional microfluidic devices. Three dimensional microfluidic devices can wick fluids laterally, within a layer of patterned paper, or vertically, between two layers of patterned paper. The layers of insulating material ensure that the fluids in different layers of patterned paper cannot mix with each other. Apertures can be provided in the layers of insulating material wherever fluids need to flow vertically between the two layers of patterned paper. Three dimensional microfluidic devices can enable two different channels to cross each other without coming into direct physical contact; this is a feature that is not possible in single layer lateral flow devices. Three dimensional devices are also useful for distributing samples into a large number of wells in any desired pattern. Three dimensional devices are useful in applications where a large number of samples are to be processed or analyzed, because samples can flow in the vertical direction, and each layer of the device can be used for sample processing or analysis. Because the layers of paper and tape are thin (~100-200 µm per layer), it is possible to stack several layers of paper and tape, without significantly changing the size of the device.

Figure 18A:
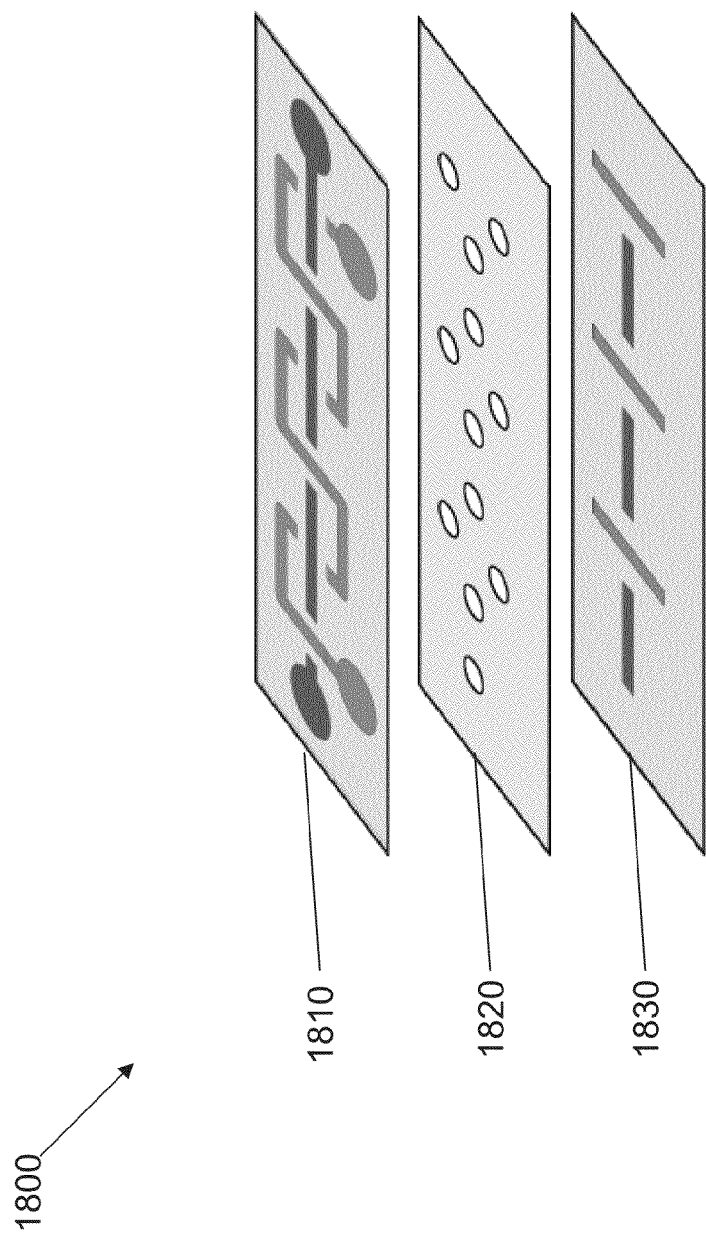
FIG. 18A illustrates a perspective view of a three-dimensional bioassay device, according to some embodiments.
Figure 18B:
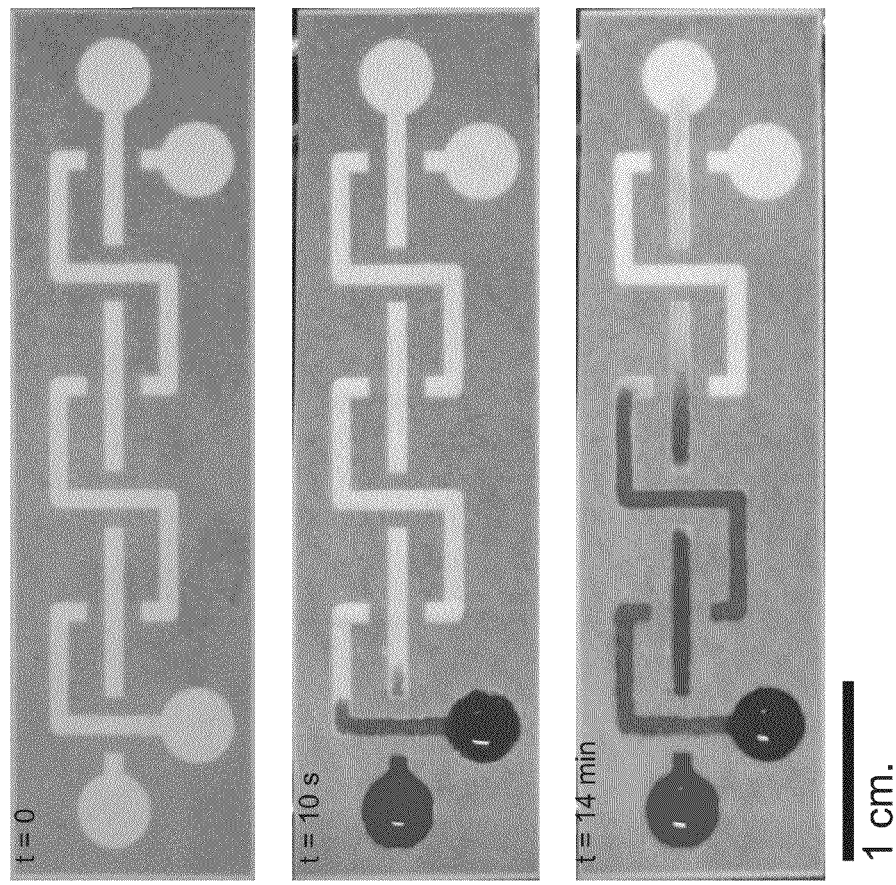
FIG. 18B shows images of an exemplary three-dimensional bioassay device at different times during exposure to colored liquids, according to some embodiments.

FIG. 18A schematically illustrates a perspective view of one embodiment of a three-dimensional microfluidic device 1800, which includes two layers of patterned paper 1810 and 1830, and one layer of insulating material 1820, e.g., double sided tape, with apertures. The three layers 1810, 1820, 1830 are aligned and bonded to each other. FIG. 18B shows device of FIG. 18A wicking aqueous dyes of two different colors (one of which appears lighter than the other, in the grayscale image). The device allows the separate channels, through which the dyes are flowing, to cross each other without any mixing taking place between the two fluids.

Figure 19:
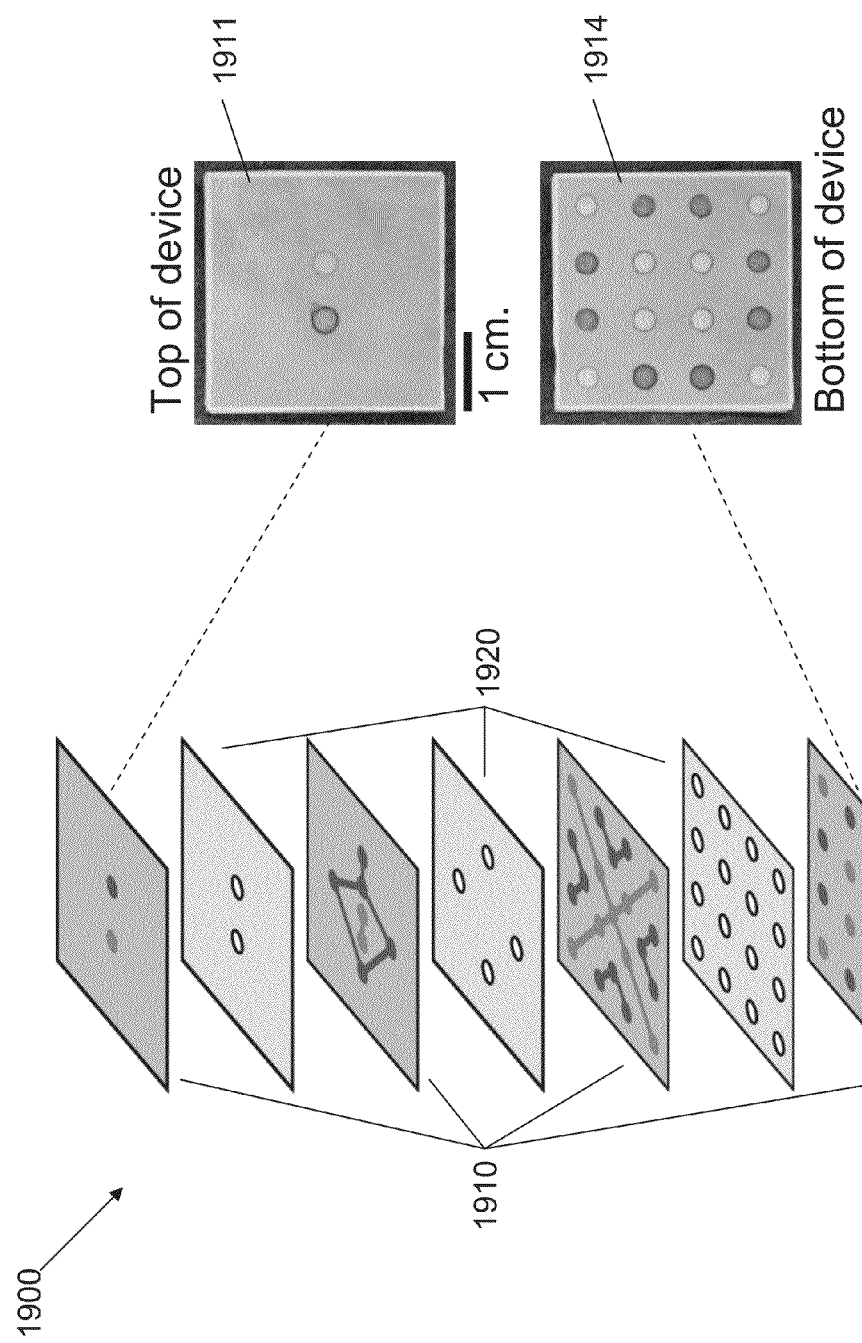
FIG. 19 illustrates a perspective view of a three-dimensional bioassay device, according to some embodiments.

FIG. 19 schematically illustrates a perspective view of another embodiment of a three-dimensional microfluidic device 1900, which is a sample distribution device designed to distribute two samples into sixteen test zones in a particular pattern. Device 1900 includes four layers of patterned paper 1910 and three layers of insulating material 1920. The top layer 1911 of the device includes two inlets for the two samples and the bottom layer 1914 of the device includes the sixteen test zones. The inner layers of the device include a plurality channels that distribute the samples in the horizontal plane. FIG. 19 schematically illustrates the flow of aqueous dyes of two different colors (one of which appears lighter than the other in the grayscale image), after applying the liquids to the two inlets on the top layer 1911 of the device, and allowing the dyes to run through device into the sixteen test zones on the bottom layer 1914. With an appropriate arrangement of channels in the inner layers of the device, any pattern of samples in the test zones can be obtained.

Methods of Providing Patterned Hydrophobic Barriers in Porous, Hydrophilic Media In some embodiments, as described in greater detail below, hydrophobic barriers can be provided in porous, hydrophilic media using patterning methods that require relatively little equipment, can be performed in nearly any laboratory, and are versatile enough for making many types of patterns and multiple copies of each pattern. Because of the relative ease of fabrication and the ready availability of inexpensive components, bioassay devices can be formed with significantly lower cost than conventional devices such as dipsticks, and thus can be useful, among other things, for detecting disease in remote locations, where resources are limited, and where cost and portability of the devices are useful.

As noted above, in order to fabricate microfluidic channels in porous, hydrophilic media, such as, but not limited to paper, the patterned hydrophobic polymer generally extends substantially through the entire thickness of the paper in order to confine the liquid within desired areas. This constraint limits the methods that can be used in practice for patterning paper. For example, printing methods using standard inks may not be suitable for making channels in paper because currently available inks are designed to adhere to the surface of paper, not to absorb into the paper. However, it can be envisioned that certain inks could be designed in order to absorb substantially through the thickness of paper.

The composition of the porous medium, e.g., paper, may also limit the patterning methods that can be used in practice. For example, paper typically includes intertwined fibers that are oriented in the x- and y-axes of a sheet of paper and that are stacked on top of one another in the z-direction. The result of this arrangement is the increased spreading of liquids in the x-, y-plane compared to the z-direction, which leads to blurring of the features that were patterned. Appropriate choices of monomers, polymers, and solvents can be made to overcome these properties of paper, and to enable the patterning of distinct features that pass through the entire thickness of paper.

Some useful methods for patterning paper are based on photolithography, and can be implemented either in a cleanroom or in a laboratory. Cleanroom photolithography works well for making highly defined patterns in paper, but is relatively expensive and slow, possibly making its commercial viability somewhat limited. Other methods, such as laboratory photolithography and soft lithography (also called micro-contact printing), eliminate the need for a cleanroom, and have only modest requirements for equipment and expertise on the part of the manufacturer, while still producing high-quality devices. Laboratory photolithography is useful for making patterns, with well-resolved channels and small feature sizes. Soft lithography is typically less expensive than the photolithographic-based methods, and is useful for making multiple copies of the same pattern relatively quickly.

For some applications, the feature sizes in paper microfluidic devices are relatively large (e.g., with channels about 1-2 mm wide), so a lower resolution, but faster stamping technique will be sufficient. For other applications, micron-sized features will be used, and so an inexpensive, but higher-resolution method will be useful. For most applications the devices will have features with sizes less than 1.5 mm. It should be recognized however that a wide variety of channel shapes and sizes can be formed using the systems and methods described herein. In both kinds of applications, it is desirable that the patterning method be inexpensive, have high-throughput, and not require a highly technically skilled user to manufacture.

The discussion below describes three methods for patterning paper (cleanroom lithography, bench-top lithography, and stamping), according to some embodiments of the invention, and compares the quality of patterns produced using each method with the cost of making them. These comparisons are made for several features that may be useful in paper microfluidic devices, e.g., curves, right angles, T-junctions, and straight channels. The widths of these features are also varied, both for the hydrophilic channels and for the hydrophobic barriers. The resolution and uniformity of these features are compared, as well as the ability of the patterns to control the spreading of water in paper. The various examples are intended to be illustrative of some types of features that can be produced using some methods, and are not to be construed as limiting the invention.

Figure 11:
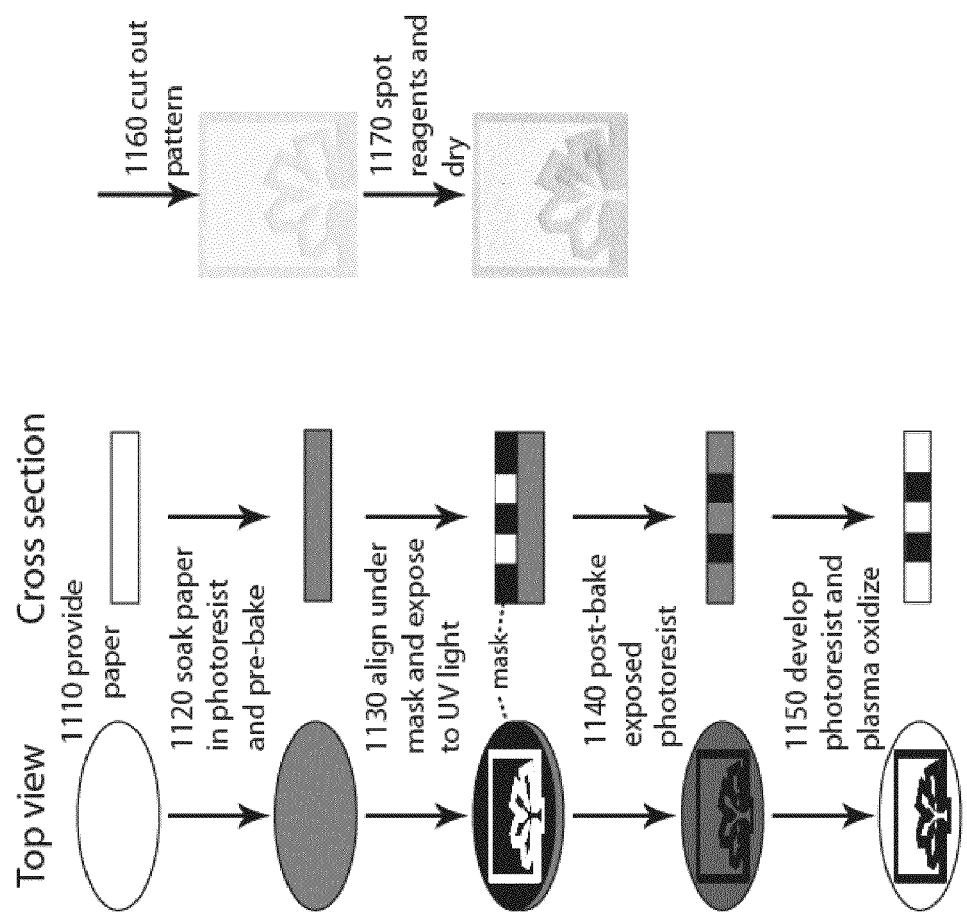
FIG. 11 illustrates an exemplary procedure for providing hydrophobic barriers in porous, hydrophilic media using photolithography in the cleanroom, according to some embodiments.

In some embodiments, hydrophobic patterns are generated using cleanroom photolithography. FIG. 11 schematically illustrates steps in an exemplary method of photolithographically patterning chromatographic paper with photoresist to create hydrophobic barriers within the paper.

In the embodiment illustrated in FIG. 11, first a porous, hydrophilic medium such as chromatography paper (e.g., about 7.5 cm in diameter and about 100 μm thick) is provided 1110. The paper is selected to have a thickness and strength sufficient to survive the lithographic steps, and also to be compatible with the subsequent intended use.

Next, the paper is soaked in photoresist and prebaked 1120. In one example, the paper is soaked in about 2 mL of SU-8 2010 photoresist for an amount of time sufficient for the photoresist to soak through the paper, e.g., 30 seconds to 1 minute. In some embodiments, the photoresist substantially permeates or impregnates the paper, so that when defined portions of the photoresist are later removed, the parts that remain on and in the paper form a substantially impermeable barrier to lateral fluid flow. Other photoactive materials that are compatible with photolithography, such as photopolymers, can also be used, so long as the material can be removed to define a pattern, without damaging the paper. The photoresist-soaked paper is then optionally spun, e.g., at 2000 rpm for 30 seconds, to remove excess photoresist. Excess photoresist can be removed in other ways, e.g., by scraping or pressing. Next, the paper is baked, e.g., at 95° C. for 5 min, or air-dried e.g., to remove cyclopentanone in the SU-8 formula.

Next, the photoresist-soaked paper is aligned under a photo-mask and exposed to UV light at a wavelength selected to cause the photoresist to react appropriately 1130. In one example, a photo-mask obtained from CAD/Art Services, Inc. is aligned using a mask aligner (OL-2 Mask Aligner, AB-M, Inc), and the paper exposed to ~405 nm UV light (50 mW/cm$^2$) through the mask for about 10 seconds. In another example, the photo-mask is printed directly onto transparencies using an inkjet printer.

Next, the exposed paper is baked 1140, e.g., at 95° C. for 5 min, to cross-link or otherwise appropriately treat the photoresist.

Next, the photoresist is developed and the resulting assembly is optionally plasma oxidized 1150. In one example, the unpolymerized photoresist is removed by soaking the exposed and post-baked paper in propylene glycol monomethyl ether acetate (PGMEA) (5 min), and by washing the pattern with 2-propanol (3×10 mL). The developing process leaves hydrophobic barriers formed of photoresist in the paper (or other porous medium). In some circumstances, following the photolithographic process, the paper has a higher hydrophobicity than it did before processing, possibly due to residual resist bound to the paper. If appropriate to achieve a satisfactory level of hydrophilicity in the paper for the intended application, the entire surface of the paper can optionally be exposed to an oxygen plasma or other appropriate treatment to adjust the hydrophilicity. In one example, the patterned paper is exposed to an oxygen plasma for 10 seconds at 600 torr (SPI Plasma-Prep II, Structure Probe, Inc). In embodiments where the paper's hydrophilicity is sufficient for the intended purpose after removing the photoresist, this step need not be performed. In some embodiments, the photoresist and processing thereof are selected to reduce or eliminate change in the hydrophilicity of the paper.

The resulting patterned paper can then be cut from the wafer to form an individual bioassay device 1160, and derivatized or otherwise modified for use in diagnostic assays by spotting reagents and drying 1170, as described in greater detail above.

The mask through which the photoresist is exposed is patterned appropriately for the desired application of the finished bioassay device. In some embodiments, the mask is patterned to define hydrophobic channels having, e.g., approximately 1 mm widths, and/or to define assay regions, e.g., between 1-10 assay regions or more, as desired. In embodiments where the device is to be used in microarray applications, the device may include more than 50, more than a hundred, or even several hundred assay regions. In embodiments including both assay regions and channels, the assay regions may be coextensive with the channel, or may branch from it. The patterned regions can have different shapes to provide information to the user regarding the type of assay, as appropriate. In general, because the paper or other porous, hydrophilic medium that occupies the channel is capable of transporting fluid through the channels by capillary action, the channels need not have a particular size or shape that is by itself capable of inducing capillary action. The smaller the channels, however, the less sample will be needed in order to make a satisfactory measurement.

Using the photolithographic methods described herein, channel widths of 100 μm have been achieved. While the smallest feature size is theoretically limited by the photolithographic resolution, some experimental parameters limit the size of the features that can practically be formed with this method. For example, because the paper is opaque and relatively thick, it typically requires a relatively long exposure time to expose the photoresist all the way through the paper, which reduces the lithographic resolution somewhat. Nonetheless, feature sizes smaller than 100 μm should be readily achievable, and much smaller features (e.g., 100 nm) are theoretically possible.

Procedures for providing hydrophobic barriers in porous, hydrophilic media using "bench-top" or "laboratory" photolithography use many of the same principles as the cleanroom photolithography described above, but are generally less expensive and simpler to perform.

Figure 12:
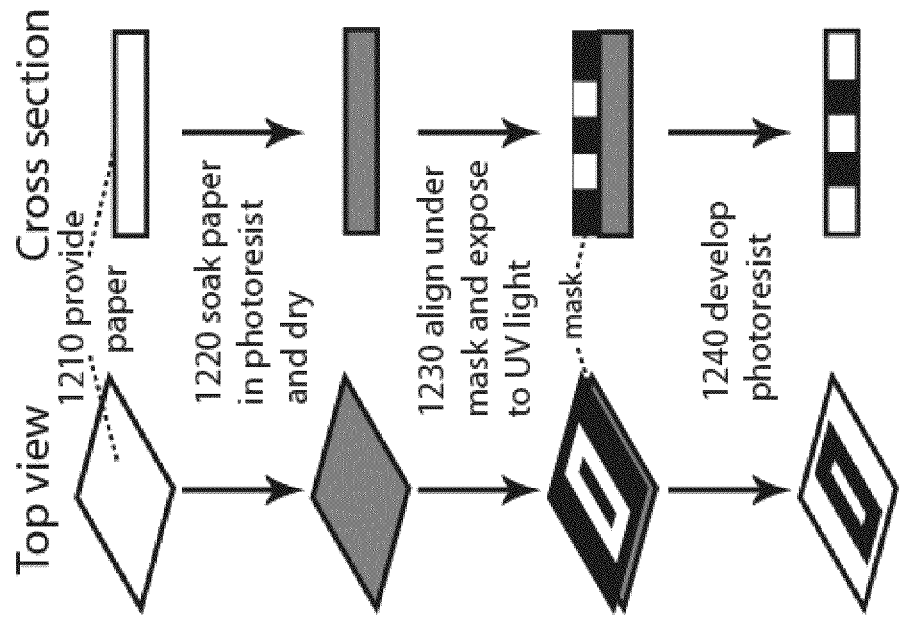
FIG. 12 illustrates an exemplary procedure for providing hydrophobic barriers in porous, hydrophilic media using photolithography in the laboratory, according to some embodiments.

FIG. 12 illustrates an exemplary process for providing hydrophobic barriers in porous, hydrophilic media according to some embodiments. First, a porous, hydrophilic medium is provided 1210. While the paper is selected to have a thickness and strength sufficient to survive the lithographic steps, and also to be compatible with the subsequent intended use, in order to reduce costs, in one example a 10 cm×10 cm piece of paper towel is used as the hydrophilic medium.

Next, the paper is soaked in photoresist and dried 1220. In one example, 1 mL of SC photoresist is spread over the paper towel using the side of a glass test tube to obtain an approximately even coating of the resist through the thickness of the paper towel. Excess resist is removed, e.g., by blotting with a paper towel, and the photoresist-soaked paper then air-dried at 25° C. for 10 min. Options for photoresist are generally the same as described with reference to FIG. 11. SC photoresist is typically less expensive than many other kinds of commercially available photoresist, and thus can be useful in cost-sensitive applications. Home-made photoresists are suitable as well.

Next, the photoresist-soaked paper is aligned under a photo-mask and exposed to UV light at a wavelength selected to cause the photoresist to react appropriately 1230. In one exemplary process, the masks for bench-top lithography are produced by printing them onto transparency sheets using a desktop inkjet printer (HP Photosmart C3100). In this example, the paper is exposed to UV light from a long wave UV lamp, B 100 AP, UVP, ~20 mW/cm$^2$, held 12 cm above the paper, for about 3.5 min through a photo-mask that is held in place on top of the paper by clamping the mask and paper between two pieces of glass. Another inexpensive source of UV light is a UV EPROM (erasable programmable read-only memory) chip erasing lamp.

Next, the photoresist is developed 1240. In one example, unpolymerized photoresist was removed by soaking the paper in xylene (3 min), and dichloromethane (3×3 min). The developing process leaves hydrophobic barriers formed of photoresist in the paper (or other porous medium). As in the embodiment of FIG. 12, the paper can be optionally treated with an oxygen plasma to adjust its hydrophilicity, e.g., by exposing the paper to an oxygen plasma for 10 seconds at 600 torr (SPI Plasma-Prep II, Structure Probe, Inc).

The resulting patterned paper can then be cut and derivatized as described in greater detail above.

Figure 13:
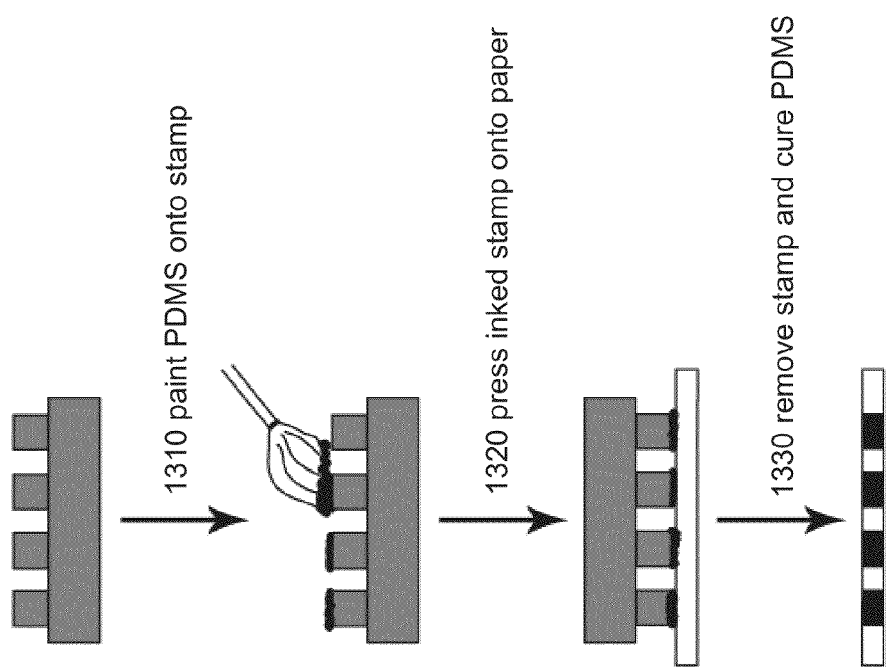
FIG. 13 illustrates an exemplary procedure for providing hydrophobic barriers in porous, hydrophilic media using microcontact printing, according to some embodiments.

In other embodiments, hydrophobic barriers are provided in porous, hydrophilic media soft lithography/microcontact printing/stamping. FIG. 13 illustrates an exemplary method for using soft lithography to provide hydrophobic barriers. First, a stamp is provided 1310. In one example, stamps are made out of plastic (Costar 384-well microplate, Corning), and in another example, rubber stamps were custom fabricated by Rubber Stamps Net, having a cost of about $25 for a 3×3 inch stamp, and are limited to features of about 0.35 mm in width. It is contemplated that other minimum feature sizes are possible, and are limited by the manufacturing technique and material used.

Next, the stamp is "inked," e.g., by painting a hydrophobic polymer onto the stamp 1320. In one example, poly(dimethylsiloxane) (PDMS) (sylgard 184, 10:1 elastomer base:curing agent, cured for 3 h at room temperature) was spread in a thin layer over the features of a pattern using a white bristle flat paintbrush #4.

Next, the polymer-inked stamp was pressed onto the porous, hydrophilic medium 1330. In one example, a PDMS-coated stamp was placed in contact with a 10×10 cm piece of paper Whatman No. 1 filter paper, pressed gently by hand for approximately 20 seconds, and the stamp then removed.

The polymer is then subsequently treated, e.g., cured 1340. Continuing the above example, the PDMS in the paper was cured for 8 h at room temperature before use.

The dimensions of the patterned features formed using the exemplary procedures described above for cleanroom lithography, laboratory/bench-top lithography, and soft lithography were quantified by imaging the patterns using a Nikon digital camera DXM1200 attached to a stereomicroscope (Leica MZ12), magnifying the images in Microsoft Powerpoint, printing the images, and measuring the features using a ruler. FIGS. 14A and 14B are images of features formed using cleanroom lithography and laboratory lithography, respectively. Table 3 summarizes the measurements made from the images; the reported values in Table 3 are calibrated for magnification, and represent real dimensions; they also are the average of 3 replicas of the same pattern measured 10 times at positions distributed throughout the entire pattern.

TABLE 3

Fidelity of transfer for two exemplary methods of patterning paper. In all cases, the hydrophilic channels and the hydrophobic walls were designed to be 1 mm.

| Method | Width of Hydrophilic Paper (mm) | | | Width of Hydrophobic Polymer (mm) |
| --- | --- | --- | --- | --- |
| | Arc | Straight Channel | 90° Angle | Straight Channel |
| Photo-lithography (cleanroom) | 1.01 ± 0.02 | 1.03 ± 0.02 | 1.03 ± 0.02 | 0.95 ± 0.01 |
| Photo-lithography (bench-top) | 0.95 ± 0.03 | 0.99 ± 0.03 | 0.99 ± 0.03 | 1.02 ± 0.03 |

Figure 16:
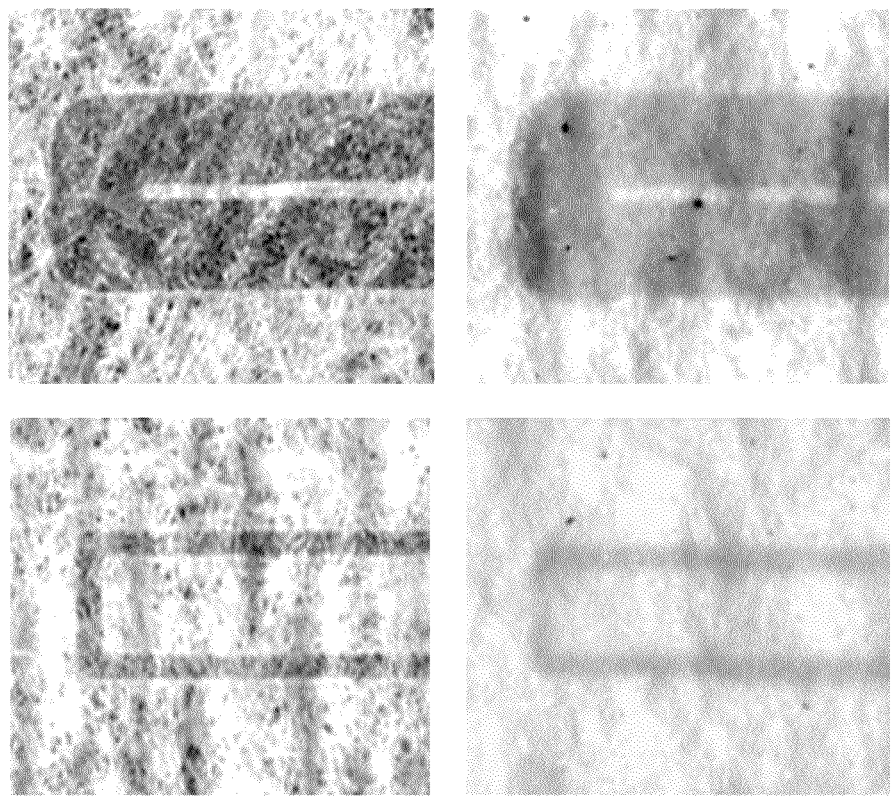
FIGS. 16A-16B are images of widths of relatively narrow barriers that provide functional devices and are formed using various methods of patterning, according to some embodiments.

The exemplary procedure for patterning hydrophobic barriers with cleanroom lithography described above with respect to FIG. 11 generates relatively well-defined features that, in some embodiments, can be made as small as about 150 μm in width for the hydrophilic channel (experimental: 158±13 μm), and about 300 μm in width for the hydrophobic walls (experimental: 297±27 μm), as shown in FIG. 16A. In general, hydrophobic walls can be made even smaller than about 150 μm, however thinner walls are less efficient at limiting the diffusion of water outside the hydrophilic channels than thicker walls.

Although cleanroom photolithography generates high-quality features, it is somewhat less efficient than bench-top lithography and bench-top stamping, in terms of throughput, expense, and the number of steps required to make a pattern. For example, in one exemplary process, cleanroom lithography uses about 0.5 g of SU-8 2010 photoresist to make a 5×5 cm grid of 3.6×3.6 mm squares on a 7.5 cm piece of filter paper (shown in FIG. 15A); this amount of photoresist alone costs ~$0.26. The exemplary fabrication process used to produce the grid shown in FIG. 15A requires nine steps before the device is complete and ready for use.

Photolithography in the cleanroom also has a practical limitation, in that the equipment is typically designed for a particular maximum size of substrate. For example, the equipment used during the exemplary process could not be used to pattern circular pieces of paper larger than 7.5 cm in diameter because the mask aligner could not accommodate larger substrates. Larger mask aligners would allow larger substrates to be patterned.

Bench-top lithography has a comparable fidelity to cleanroom lithography for transferring features from a mask to a piece of paper when the features are millimeters in size. For example, as shown in Table 3, a mask with hydrophilic channels and hydrophobic walls of 1 mm gives patterns in paper that are 0.99±0.03 mm wide for the channels and 1.02±0.03 mm wide for the walls.

Bench-top lithography, however, may be somewhat less consistent than cleanroom lithography at providing features of equal size throughout a pattern. For example, in some embodiments the line width has 50% higher variation for bench-top lithography than cleanroom lithography. Bench-top lithography may also be less efficient than cleanroom lithography at producing patterns with relatively narrow line widths. For example, using the exemplary processes described above, the narrowest features made that did not leak using bench-top lithography were about 100 μm in width (experimental value 106±23 μm) (for the hydrophilic channel), and about 150 μm in width (experimental value 245±31 μm) (for the hydrophobic walls), as shown in FIG. 16B.

Bench-top lithography, however, is significantly less expensive and higher throughput than cleanroom lithography. In one exemplary process using bench-top lithography, 0.5 g of SC photoresist was used to make a 10.7×7.2 cm grid of 3.6×3.6 mm squares (FIG. 15B), which costs ~$0.05 ($0.21 less than with cleanroom lithography).

The same resist could be used in the cleanroom process as well, so one useful feature of the bench-top method is not in the cost of the resist, but in the cost of the equipment and in the throughput for the process. For example, in some exemplary processes, making the same 5×5 cm grid on the bench top requires 6 steps (3 fewer than the cleanroom process), and can be accomplished ~10 min faster than the time required to make the grid in the cleanroom.

In some embodiments, the stamping method is an easier and cheaper method of patterning paper than cleanroom or bench-top photolithography, but may yield somewhat lower quality patterns. The quality of the stamp itself, in addition to the transfer process, can affect the quality of the resulting pattern. While the exemplary processes describe above used commercially-bought stamps, stamps can also be made in the laboratory, e.g., using poly(dimethylsiloxane) (PDMS) by replica molding a master (made by photolithography), using techniques known in the art.

In some embodiments, the stamping method is significantly less expensive than the photolithographic methods. In one exemplary process, a 10.7×7.2 cm grid of 3.6×3.6 mm squares (FIG. 15C) can be made in about 120 seconds using only 0.1 g of PDMS (which costs ~$0.01, and is $0.25 and $0.04 less expensive than the polymers used to make the same pattern by exemplary bench-top or cleanroom lithographic methods, respectively).

Embodiments of the stamping method also allow a wide variety of materials. The technique has been demonstrated for generating patterns, for example, using PDMS, paraffin wax (m.p. 58-60° C.), and Norland optical adhesive (NOA), a urethane-based adhesive that can be cured with UV light (Norland Products, Inc.).

Table 4 includes information comparing the estimated costs to pattern porous, hydrophilic media with hydrophobic barriers, according to various exemplary embodiments. The cost of the relatively high-resolution methods (cleanroom photolithography and bench-top photolithography) can be reduced, for example, by using relatively inexpensive negative photoresist (e.g., SC photoresist, Arch Chemicals, Inc.), by printing masks using an inkjet printer (e.g., instead of buying them from a printing service), and/or exposing the photoresist using a standard 100 W mercury lamp (e.g., Blak-ray long wave UV lamp B100 AP, approximately $514). For producing multiple copies of a single pattern with relatively low-resolution (wide) features, stamps (rubber or plastic) can be used, that can be purchased from suppliers in almost any design desired (the rubber stamps cost ~$25). In some embodiments, poly(dimethylsiloxane) (PDMS) is used as the hydrophobic polymer. Various porous media are also compared, e.g., Kimberly-Clark hard roll paper towels and Whatman No. 1 filter paper, though similar results likely will be obtained with other papers as well. Kimberly-Clark paper towels are a relatively inexpensive source of paper available that wicks fluids well.

TABLE 4

Comparison of the equipment needed and expenses incurred for three exemplary methods of patterning porous media with hydrophobic barriers

| Method | Components[a] | Pieces of Equipment | Time Required to Make 1 Replica (min) | Cost of Polymer For 1 Replica[d] |
|---|---|---|---|---|
| Photolithography (cleanroom) | 1. silicon wafer 2. SU-8 2010 photoresist 3. spin coater 4. hot plate 5. mask aligner 6. 1000 W mercury lamp | 5 | ~40[b] | $0.26 |
| Photolithography (bench-top) | 1. SC photoresist 2. hot plate 3. 100 W mercury lamp | 3 | ~30[c] | $0.05 |
| Stamping | 1. stamp 2. PDMS | 1 | ~2[d] | $0.01 |

[a]All methods use Kimberly-Clark hard roll paper towels or Whatman No. 1 filter paper.
[b]It takes an additional 10 minutes to make a second replica.
[c]It takes an additional approx. 8 minutes to make a second replica.
[d]This time estimate does not include the time required for the patterns to dry.
[d]This cost estimate is only for the cost of the polymer (photoresist or PDMS); it does not include the cost of the paper, the solvent, or the use of electricity.

Other methods can also be used to form hydrophobic barriers in the porous, hydrophilic medium. For example, liquids may be applied to the medium in accordance with a pattern. The liquid may itself be hydrophobic, or may be capable of change to a hydrophobic solid upon drying or upon further treatment. For example, the liquid may be a commercially available waterproofing solution, which is hydrophilic and thus will wet the paper but forms a hydrophobic solid upon drying, or the liquid may be a monomer, which upon polymerization forms a hydrophobic solid.

The liquid may be applied in accordance with a pattern in many different ways. For example, the liquid may be sprayed, e.g., airbrushed, or otherwise deposited through a stencil. Or, for example, the liquid may be deposited using well-known "silk screening" techniques. Alternately, a lithographically patterned piece of paper can be used as a "stamp" for another piece of paper. For example, the patterned piece of paper can be lithographically patterned, e.g., as described above, to create hydrophobic and hydrophilic regions. The patterned paper can then be soaked with a liquid so that only designated parts of the paper, typically the hydrophilic parts, are wetted by the solution. The patterned and soaked paper is then brought into contact with another (unpatterned) piece of paper, which the liquid soaks into, thus transferring the pattern. Ink jet printing is another method that can be used to deposit liquid on the paper in accordance with a pattern. Alternatively, a plotter can be used to "draw" a pattern on the paper. A common feature of the above-described embodiments is the need to deposit sufficient liquid onto the paper to substantially permeate it, to create a barrier to lateral fluid flow across the patterned region.

One factor that may limit resolution size when applying a liquid to the paper in accordance with a pattern, is that the liquid may also flow laterally as it soaks through the thickness of the paper, thus blurring the edges of the intended feature. This problem can be alleviated somewhat by applying a vacuum to the bottom surface of the paper which can speed the transport of the liquid through the paper thickness, thus limiting the amount of time the liquid can laterally spread.

Wax is one inexpensive, readily available alternative to photoresist that can potentially be used to form hydrophobic channels within the chromatographic paper. For example, wax from wax paper can be transferred to the chromatographic paper in accordance with a pattern. In some embodiments, this is done by sandwiching the paper to be patterned between two pieces of wax paper, and the desired pattern "written" on the wax paper using a heated instrument. This process transfers a small amount of wax from the two pieces of wax paper onto both sides of the paper. The paper can then be heated on a hotplate to melt the wax through the thickness of the paper, creating a hydrophobic barrier. Or, for example, a thread soaked in wax can be stitched through the chromatographic paper in accordance with a pattern, and the wax subsequently melted so that it locally saturates the paper.

It will be appreciated that the scope of the present invention is not limited to the above-described embodiments, and that the invention encompasses modifications of and improvements to what has been described. Other embodiments are within the scope of the following claims.

What is claimed is:

1. An assay device comprising:
   a plurality of porous, hydrophilic media in the form of substantially planar sheets disposed face-to-face and separated from each other by a fluid-impermeable layer which defines an opening for fluid communication between adjacent sheets,
   a said sheet comprising a pattern of fluid-impervious barriers substantially inserting through the thickness of the sheet thereby to define a boundary of an assay region comprising a channel region defining a flow path within the sheet through which fluids pass, and
   one or more assay reagents disposed in fluid communication with the assay region which provide an indication in the device of a clinically relevant presence or concentration of an analyte.

2. The assay device of claim 1 comprising a said channel region defining a flow path along which fluids pass in a direction parallel to the plane of a sheet by capillary action.

3. The assay device of claim 1 or 2 comprising a channel region defining a flow path including a said opening through which fluid flows between adjacent sheets.

4. The device of claim 1, said pattern of fluid-impervious barriers defining boundaries of plural assay regions comprising plural flow paths through which fluids pass within said device, one or more said assay reagents being disposed in fluid communication with the respective assay regions which alone or together provide an indication in the device of a clinically relevant presence or concentration of one or more analytes.

5. The assay device of claim 1 or 4 wherein the assay reagent(s) provide a visible indication of a clinically relevant presence or concentration of an analyte which can be digitized to reproduce an image of said visual indication which also is clinically relevant.

6. The device of claim 5 which provides a visible indication of the concentration of an analyte.

7. The device of claim 4 comprising at least two flow paths, not in fluid communication with each other, through which fluids pass and which cross each other without mixing of fluids.

8. The device of claim 1 or 4 comprising multiple said flow paths through which fluids pass and which distribute analyte to a plurality of separated test zones.

9. The device of claim 8 comprising different assay reagents disposed in fluid communication with the separated test zones which different assay reagents provide a visible indication of the presence or concentration of one or more analytes in subsets or individual zones of said plurality of separated test zones.

10. The device of claim 1 wherein a said hydrophilic medium and a barrier together define a reservoir for receiving a first fluid, said device further comprising one or more distributing regions for receiving said first fluid from said reservoir, and a plurality of separated test zones for receiving said first fluid from said distributing regions.

11. The device of claim 10 further comprising different assay reagents disposed in a said medium for assaying said fluid in, or in fluidic communication with, different test zones.

12. The device of claim 1 further comprising a sample deposition region bounded by a said fluid-impervious barrier or by an opening in a fluid-impermeable layer disposed in face-to-face relation with a said sheet, and in fluid communication with a said flow path.

13. The device of claim 12 wherein said sample deposition region comprises a porous, hydrophilic medium.

14. The device of claim 12 further comprising a filter in fluid communication with said sample deposition region.

15. The device of claim 1 wherein said porous, hydrophilic sheet comprises a material selected from the group consisting of polymer film, nitrocellulose acetate, cellulose acetate, fibrous material, paper, and cloth.

16. The device of claim 1 wherein said barrier comprises a material selected from the group consisting of a curable polymer, polymerized photoresist, wax, and poly(dimethyl-siloxane).

17. The device of claim 1 wherein the assay reagent is selected to react to the presence of at least one of glucose, a protein, and a fat.

18. The device of claim 4 wherein said barriers physically separate individual zones of said plural assay regions from one another.

19. The device of claim 1 further comprising an imaging device which obtains a digital image of the visible indication of a clinically relevant presence or concentration of an analyte.

20. The device of claim 19 further comprising a processor in communication with the imaging device and capable of obtaining information about an analyte in the assay region based on the digital image of the assay region.

21. The assay device of claim 20 wherein the processor obtains information about the analyte based on a color intensity or position of a feature in the digital image.

* * * * *

UNITED STATES PATENT AND TRADEMARK OFFICE
CERTIFICATE OF CORRECTION

PATENT NO. : 8,603,832 B2
APPLICATION NO. : 13/730028
DATED : December 10, 2013
INVENTOR(S) : George M. Whitesides et al.

Page 1 of 1

It is certified that error appears in the above-identified patent and that said Letters Patent is hereby corrected as shown below:

In the Specification

In Column 1, starting at Line number 25, please replace the existing paragraph with the following:
This invention was made with government support under GM065364 awarded by National Institutes of Health (NIH) and under 0213805 awarded by National Science Foundation (NSF). The government has certain rights in this invention.

Signed and Sealed this
Sixteenth Day of September, 2025

Coke Morgan Stewart
*Acting Director of the United States Patent and Trademark Office*